United States Patent
Farran et al.

(10) Patent No.: US 12,186,417 B2
(45) Date of Patent: *Jan. 7, 2025

(54) SKIN PERFECTING COSMETIC COMPOSITIONS AND METHODS OF USE

(71) Applicant: L'OREAL, Paris (FR)

(72) Inventors: Alexandra Jane Farran, Dayton, NJ (US); Anne-Laure Suzanne Bernard, New-York, NY (US); Cynthia Ghobril, Paris (FR); Julie Martin-Besnardiere, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/934,349

(22) Filed: Sep. 22, 2022

(65) Prior Publication Data

US 2023/0036740 A1 Feb. 2, 2023

Related U.S. Application Data

(63) Continuation of application No. 16/289,204, filed on Feb. 28, 2019, now Pat. No. 12,011,494.

(51) Int. Cl.
| | |
|---|---|
| *A61K 8/31* | (2006.01) |
| *A61K 8/81* | (2006.01) |
| *A61K 8/891* | (2006.01) |
| *A61Q 19/08* | (2006.01) |

(52) U.S. Cl.
CPC .............. *A61K 8/31* (2013.01); *A61K 8/8152* (2013.01); *A61K 8/891* (2013.01); *A61Q 19/08* (2013.01); *A61K 2800/31* (2013.01); *A61K 2800/43* (2013.01); *A61K 2800/48* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 5,817,426 | A | * 10/1998 | Spada | C09J 4/00 428/483 |
| 6,103,250 | A | * 8/2000 | Brieva | A61K 8/26 514/474 |
| 9,918,925 | B2 | 3/2018 | Debeaud et al. | |
| 2008/0014235 | A1 | 1/2008 | Lion et al. | |
| 2014/0242014 | A1 | 8/2014 | Bukawa et al. | |
| 2017/0172883 | A1 | 6/2017 | MacNeill et al. | |
| 2017/0231894 | A1 | 8/2017 | Daubersies et al. | |
| 2017/0290747 | A1 | 10/2017 | Bouarfa et al. | |
| 2017/0360682 | A1 | 12/2017 | Debeaud et al. | |
| 2018/0015023 | A1 | 1/2018 | Bernard et al. | |
| 2018/0116944 | A1 | 5/2018 | Halpern Chirch et al. | |
| 2019/0029943 | A1 | 1/2019 | Bernard et al. | |

FOREIGN PATENT DOCUMENTS

| | | | | |
|---|---|---|---|---|
| EP | 0972512 | A1 * | 6/1999 | ............ A61K 8/895 |
| FR | 3030265 | A1 * | 6/2016 | |
| KR | 100797072 | B1 | 1/2008 | |
| WO | WO-0247639 | A2 * | 6/2002 | ............... A61K 8/28 |
| WO | WO-2012084522 | A2 * | 6/2012 | ........... A61K 8/0241 |
| WO | 2015126874 | A1 | 8/2015 | |
| WO | 2016100690 | A1 | 6/2016 | |
| WO | 2017117426 | A1 | 7/2017 | |

OTHER PUBLICATIONS

EP0972512 Eng Tran. Published: Jun. 28, 1999.*
FR3030265 Eng Tran. Published: Jun. 24, 2016.*
International Search Report and Written Opinion issued on May 20, 2020 for corresponding PCT Application No. PCT/US2020/018536.
Emulsion Dictionary Dot Com. https://www.dictionary.com/browse/emulsion. Copyright 2022.
Emulsion Cambridge English Dictionary. https://dictionary.cambridge.org/us/dictionary/english/emulsion. Copyright 2022.

* cited by examiner

*Primary Examiner* — Nicole P Babson
*Assistant Examiner* — Lori K Mattison
(74) *Attorney, Agent, or Firm* — POLSINELLI PC

(57) ABSTRACT

The instant disclosure relates to cosmetic compositions that when applied to skin instantaneously and dramatically improve the appearance of the skin. The compositions include volatile hydrocarbon oil; mineral thickening agents; silicone elastomers; and hydrophobic film forming polymers; wherein the weight ratio of the total amount of hydrophobic film forming polymers to the total amount of mineral thickeners (film forming polymers:mineral thickening agent) is 1:1 to 8:1, and the weight ratio of the total amount of silicone elastomer to the total amount of mineral thickener (silicone elastomer:mineral thickening agent) is 1:1 to 5:1. Methods for improving the appearance of skin comprising application of the cosmetic compositions to the skin are also disclosed.

20 Claims, No Drawings

SKIN PERFECTING COSMETIC COMPOSITIONS AND METHODS OF USE

CROSS-REFERENCE TO RELATED APPLICATIONS

This application claims priority to and is a continuation of U.S. patent application Ser. No. 16/289,204, filed on Feb. 28, 2019, entitled "SKIN PERFECTING COSMETIC COMPOSITIONS AND METHODS OF USE," the entirety of which is herein incorporated by reference.

FIELD OF THE DISCLOSURE

The present disclosure relates to cosmetic compositions for application to the skin for providing an instantaneous and dramatic improvement to the appearance of skin, for example, by reducing the appearance of wrinkles, eye bags, pores, and skin imperfections such as scarring, dark spots (and uneven skin tone), dark circles, and roughness.

BACKGROUND

Skin produces less collagen and elastin as it ages. For example, after the age of twenty, a person (human) produces about 1 percent less collagen in the skin each year. As a result, the skin becomes thinner and more fragile. Inevitably, wrinkles, crow's feet, age-spots, eye bags, and the like, begin to form.

Consumers often wish to improve the appearance of such age-related skin imperfections, preferably with instantaneous results. Many consumer products and procedures devoted to hiding and reducing wrinkles are available. Some products and procedures are simple and inexpensive, for example, applying make-up, particularly a primer or colored foundation, to cover the skin (and thereby cover and/or fill the wrinkles and provide a smoother look). Far more expensive and drastic procedures, such as surgical face lifts and Botox® injections, are also used to reduce the appearance of wrinkles. However, many consumers either cannot afford, or do not wish, to undergo such drastic cosmetic procedures. There are a number of lotions and creams which are formulated to hydrate the skin and make it more supple, thereby reducing the appearance of wrinkles. Some of these products contain active ingredients, for example, niacinamide, that help repair and rejuvenate skin over time. Unfortunately, however, all of these products and procedures have drawbacks.

Make-up products are often visible, offer minimal texture benefits, and have no long-term lasting effect on the skin. After removal of the make-up, the skin looks the same as before the make-up was applied. Common skin care products can have chronic, acute or both effects on the skin. Hydration and optical effects are common acute benefits, but these benefits quickly wear-off over time.

Attempts have been made to develop new categories of products to improve the appearance of skin without the drawbacks of existing products and procedures. One such family of products can be generally classified as "adhesive, contractile film formers". Film formers are chemical compositions that when applied to skin, leave a pliable, cohesive and continuous covering. A select group of film formers are also adhesive to the skin and contractile.

SUMMARY OF THE DISCLOSURE

The instant disclosure relates to skin perfecting cosmetic compositions, i.e., cosmetic compositions that are applied to the skin and improve the appearance of the skin. The compositions include a combination of ingredients such as volatile hydrocarbon oil, mineral thickening agents, silicone elastomers, and hydrophobic film forming polymers, which combine to form unique compositions that instantaneously and dramatically improves the appearance of skin. For example, upon application to the skin, the compositions reduce the appearance of wrinkles, eye bags, pores, and skin imperfections such as scarring, dark spots (and uneven skin tone), dark circles (typically around the eyes), and roughness. Unlike other products, the films formed on the skin are particularly long lasting, and are not prone to dry-out, whitening, cracking, or peeling. Instead, they remain flexible (elastic), durable, and comfortable. Moreover, the compositions (and resulting films) hydrate and protect the underlying skin.

The cosmetic compositions of the instant disclosure typically include:
  about 40 to about 85 wt. % of one or more volatile hydrocarbon oils;
  at least 1 to about 10 wt. % of one or more mineral thickening agents;
  about 1 to about 20 wt. % of one or more silicone elastomers; and
  at least 5 wt. % of one or more hydrophobic film forming polymers;
  all percentages by weight are based on the total weight of the cosmetic composition.

The weight ratio of the total amount of hydrophobic film forming polymers to the total amount of mineral thickening agent (film forming polymers: mineral thickening agent) is typically about 1:1 to about 8:1; and/or the weight ratio of the total amount of silicone elastomer to the total amount of mineral thickening agent (silicone elastomer: mineral thickening agent) is typically about 1:1 to about 5:1.

Addition ingredients may also optionally be included in the cosmetic compositions. Non-limiting examples include water, non-volatile fatty substances, inorganic pigments, soft focus particles/powders, fragrances, preservatives, coalescents, wetting agents, water-soluble solvents, emollients, suspending agents, surfactants, actives, etc. One unique feature of the cosmetic compositions is that they may include water (aqueous compositions) or may be free of water (anhydrous compositions).

Non-limiting examples of volatile hydrocarbon oils include those having from 8 to 16 carbon atoms, for example, linear or branches alkanes. Useful branched alkanes include, but are not limited to, isoparaffin, isohexadecane, isododecane, isodecane, undecane, tridecane, dodecane, and a mixture thereof.

Non-limiting examples of mineral thickening agents include silica silylate, fumed silica, zeolite, natural clay, synthetic clay, kaolin, hectorite, organically modified hectorite (e.g., INCI: pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite), and a mixture thereof.

The silicone elastomers can be non-emulsifying silicone elastomers, emulsifying silicone elastomers, or a mixture thereof. Non-emulsifying silicone elastomers include, but are not limited to, those organopolysiloxane elastomers not containing a hydrophilic chain, such as polyoxyalkylene or polyglycerolated chains. On the other hand, emulsifying silicone elastomers include, but are not limited to, polyoxyalkylenated silicone elastomers and a polyglycerolated silicone elastomers.

Non-limiting examples of hydrophobic film-forming polymers include trimethylsiloxysilicate, acrylates/isobornyl acrylate copolymer, acrylic acid/isobutyl acrylate/isobornyl acrylate copolymer, acrylate/polytrimethyl siloxymethacrylate copolymer, C30-45 alkyldimethylsilylpolypropylsilsequixane, trimethylsilsesquixane, polypropylsilsesquixane, acrylates/dimethicone copolymer, octylacrylamide/acrylates/butylaminoethyl methacrylate copolymer, VA/butyl maleate/isobornyl acrylate copolymer, acrylates/t-butylacrylamide copolymer, polyvinylpyrrolidone/vinyl acetate copolymer, triacontanyl PVP copolymer, acrylates/dimethylaminoethyl methacrylate copolymer, and a mixture thereof. In some instances, a particularly useful hydrophobic film forming polymer is acrylic acid/isobutyl acrylate/isobornyl acrylate copolymer.

The instant disclosure also relates to methods for improving the appearance of skin comprising applying the compositions described herein to the skin. In some instances, the compositions are applied to the skin of the face and/or neck and may be specifically applied around the eyes, around the mouth, and/or around the neck of a human face. The methods of improving the appearance of skin include methods for treating or reducing the appearance of wrinkles, blemishes, dryness, roughness, dullness, age spots, discoloration, scarring, sagging, and/or puffy skin.

DETAILED DESCRIPTION OF THE DISCLOSURE

The instant disclosure relates to cosmetic compositions that provide an instantaneous and dramatic improvement to the appearance of skin, in particular, the skin of the face. The cosmetic compositions typically include:
  about 30 to about 85 wt. % of one or more volatile hydrocarbon oils;
  about 1 to about 20 wt. % of one or more mineral thickening agents;
  about 1 to about 40 wt. % of one or more silicone elastomers; and
  at least 5 wt. % of one or more hydrophobic film forming polymers;
  wherein the weight ratio of the total amount of hydrophobic film forming polymers to the total amount of mineral thickening agent (film forming polymers: mineral thickening agent) is 1:1 to 8:1;
  the weight ratio of the total amount of silicone elastomer to the total amount of mineral thickening agent (silicone elastomer: mineral thickening agent) is 1:1 to 5:1; and
  all percentages by weight are based on the total weight of the cosmetic composition.

Suitable volatile hydrocarbon oils, mineral thickening agents, silicone elastomers, and hydrophobic film forming polymers are described in more detail below, under their respective headings. The cosmetic composition may also optionally include (or optionally exclude), for example, one or more non-volatile fatty substances, inorganic pigments, organic colorants, soft focus powder, water-soluble solvents, non-mineral thickening agents, surfactants (i.e., nonionic, amphoteric, anionic, or cationic), preservatives, fragrances, salts, etc. Many of these optionally constituents are described in more detail below, under their respective headings.

As noted above, the weight ratio of the total amount of hydrophobic film forming polymers to the total amount of mineral thickening agent (film forming polymers: mineral thickening agent) is 1:1 to 8:1. The ratio, however, may be greater than 1:1 (e.g., 1.1:1 or 1.2:1) to 8:1, i.e., the total amount of hydrophobic film forming polymers is greater than the total amount of mineral thickening agent. In some instances, the ratio of the total amount of hydrophobic film forming polymers to the total amount of mineral thickening agent (film forming polymers: mineral thickening agent) is 1:1 to 7:1, 1:1 to 6:1, 1:1 to 5:1, 2:1 to 8:1, 2:1 to 7:1, 2:1 to 6:1, or 2:1 to 5:1.

The weight ratio of the total amount of silicone elastomers to the total amount of mineral thickening agent (silicone elastomer: mineral thickening agent) is 1:1 to 5:1. The ratio, however, may be greater than 1:1 (e.g., 1.1:1 or 1.2:1) to 5:1, i.e., the total amount of silicone elastomers is greater than the total amount of mineral thickening agent. In some instances, the ratio of the total amount of silicone elastomers to the total amount of mineral thickening agent is 1:1 to 4:1, 1:1 to 3.5:1, 1:1 to 3:1, 1.1:1 to 4:1, 1.1 to 3.5:1, 1.1:1 to 3:1, 1.2:1 to 4:1, 1.2:1 to 3.5:1, or 1.2:1 to 3:1.

A unique and surprising aspect of the instant compositions is their ability to be formulated as aqueous compositions or as anhydrous (or essentially anhydrous) compositions. In some instances, the cosmetic compositions are anhydrous or essentially anhydrous (or substantially anhydrous). The term "essentially anhydrous" or "substantially anhydrous" means that the composition includes less than 5% by weight of water. Nonetheless, the composition may include less than about 4 wt. %, less than about 3 wt. %, less than about 2 wt. %, less than about 1 wt. %, less than about 0.5 wt. %, less than about 0.1 wt. % of water, less than about 0.05 wt. % water, or less than 0.01 wt. % water.

When the cosmetic compositions are aqueous compositions, the total amount of water in the cosmetic composition can vary but is typically 5 to about 40 wt. %, based on the total weight of the cosmetic composition. The total amount of water may be 5 to about 35 wt. %, 5 to about 30 wt. %, 5 to about 25 wt. %, 5 to about 20 wt. %, about 6 to about 40 wt. %, about 6 to about 35 wt. %, about 6 to about 30 wt. %, about 6 to about 25 wt. %, about 6 to about 20 wt. %, about 8 to about 40 wt. %, about 8 to about 35 wt. %, about 8 to about 30 wt. %, about 8 to about 25 wt. %, or about 8 to about 20 wt. %, based on the total weight of the cosmetic composition.

The cosmetic compositions may be in the form of a crème, a gel, a lotion, a serum, a paste, and the like. When the cosmetic compositions include water, they may be in the form of an emulsion, for example, a water-in-oil emulsion or an oil-in-water emulsion. In some instances, a water-in-oil emulsion is preferred.

The viscosity of the cosmetic compositions can vary. Nonetheless, in some instances, the viscosity is about 0.1 Pa·s to about 10,000 Pa·s at 25° C., and shear rate of 1 s$^{-1}$ at 25° C. The viscosity measurements can be carried out, for example, using a TA Instruments Rheometer, Model Discovery HR-3 (TA Instruments, New Castle DE), with a 40 mm/2 degrees standard steel cone plate, and a flow procedure consisting of ramping the shear rate from 0.01 s$^{-1}$ to 1000 s$^{-1}$ at 25° C., following a conditioning step of 0.1 rad/sec for 30 sec at 25° C. In some instances, the viscosity is about 0.1 Pa·s to about 8,000 Pa·s, about 0.1 Pa·s to about 5,000 Pa·s, about 0.1 Pa·s to about 2,000 Pa·s, about 1 Pa·s to about 10,000 Pa·s, about 1 Pa·s to about 8,000 Pa·s, about 1 Pa·s to about 5,000 Pa·s, about 1 Pa·s to about 2,000 Pa·s, about 1 Pa·s to about 1,000 Pa·s, about 25 Pa·s to about 10,000 Pa·s, about 25 Pa·s to about 8,000 Pa·s, about 25 Pa·s to about 5,000 Pa·s, about 25 Pa·s to about 2,000 Pa·s, or about 25 Pa·s to about 1,000 Pa·s.

Volatile Hydrocarbon Oils

The term "oil" is understood to mean a compound which is liquid at ambient temperature (25° C.) and normal pressure (1 atm), and which, when it is introduced in a proportion of at least 1% by weight into water at 25° C. is not soluble in water or soluble to a level of less than 10% by weight, with respect to the weight of oil introduced into the water.

The term "hydrocarbon oil" is oil comprising hydrogen and carbon atoms, and containing no silicon atoms.

The term "volatile hydrocarbon oil" is a hydrocarbon oil that is volatile at ambient temperature (25° C.) and normal pressure (1 atm) and may include, for example, isododecane, isohexadecane, hydrogenated polyisobutene.

Suitable volatile hydrocarbon oils include, but are not limited to, those having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of ISOPAR or PERMETHYL, the $C_8$ to $C_{16}$ branched esters such as isohexyl or isodecyl neopentanoate and their mixtures. Preferably, the volatile hydrocarbon oils have a flash point of at least 40° C. In some instances, isododecane and/or isoparaffins (e.g., C8-9 isoparaffin) are particularly preferred.

The total amount of the volatile hydrocarbon oils may vary but is typically about 30 to about 85 wt. %, based on the total weight of the cosmetic composition. In some cases, the total amount of volatile hydrocarbon oils is about 30 to about 80 wt. %, about 30 to about 75 wt. %, about 35 to about 85 wt. %, about 35 to about 80 wt. %, about 35 to about 75 wt. %, about 40 to about 85 wt. %, about 40 to about 80 wt. %, or about 40 to about 75 wt. %, based on the total weight of the cosmetic composition.

Mineral Thickening Agents

Mineral thickening agents are mineral based compounds that thicken or modify the viscosity of the cosmetic compositions. Non-limiting examples of mineral thickening agents include silica silylate, fumed silica, zeolite, natural clay, synthetic clay, kaolin, hectorite, organically modified hectorite (e.g., INCI: pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite), and a mixture thereof.

In some instances, the cosmetic compositions may include one or more mineral thickening agents selected from optionally modified silicas, optionally modified clays, and a mixture thereof. The mineral thickening agents may preferably be selected from optionally modified silicas, optionally modified clays, and a mixture thereof. In some instance, the mineral thickening agents are chosen from lipophilic (organophilic) clays, in particular modified hectorites; hydrophobic-treated fumed silica; hydrophobic silica aerogels, and mixtures thereof (e.g., disteardimonium hectorite, silica silicate, or a mixture thereof).

The total amount of the mineral thickening agents in the cosmetic compositions may vary but is typically about 1 to about 20 wt. %, based on the total weigh of the cosmetic composition. The total amount of the mineral thickening agents may be about 1 to about 15 wt. %, about 1 t about 10 wt. %, about 1 to about 8 wt. %, about 1 to about 5 wt. %, about 2 to about 20 wt. %, about 2 to about 15 wt. %, about 2 to about 10 wt. %, about 2 to about 8 wt. %, or about 2 to about 5 wt. %, based on the total weight of the cosmetic composition.

i) Optionally Modified Silicas

Optionally modified silicas include fumed silica optionally subjected to a hydrophobic surface treatment, the particle size of which may be less than 1 μm. Specifically, it is possible to chemically modify the surface of the silica, by chemical reaction generating a reduced number of silanol groups present at the surface of the silica. Silanol groups can in particular be replaced by hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as "silica silylate" according to the CTFA (6th edition, 1995). They are sold, for example, under the references AEROSIL R812 by the company Degussa, and CAB-O-SIL TS-53 by the company Cabot, dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold, for example, under the references AEROSIL R972 and AEROSIL R974 by the company Degussa, and CAB-O-SIL TS-610 and Cab-O-Sil TS-720 by the company Cabot.

The hydrophobic fumed silica in particular may have a particle size that is nanometric to micrometric, for example ranging from about 5 to 200 nm.

The optionally modified silicas may, for instance, be silica aerogel particles. Silica aerogels are porous materials obtained by replacing (by drying) the liquid component of a silica gel with air. They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles may have a specific surface area per unit mass ($S_M$) ranging from 500 to 1500 m$^2$/g, preferably from 600 to 1200 m$^2$/g and better still from 600 to 800 m$^2$/g, and a size expressed as the volume mean diameter (D[0.5]) ranging from 1 to 1500 μm, better still from 1 to 1000 μm, preferably from 1 to 100 μm, in particular from 1 to 30 μm, more preferably from 5 to 25 μm, better still from 5 to 20 μm, and even better still from 5 to 15 μm. In some instances, the hydrophobic silica aerogel particles have a size expressed as volume-mean diameter (D[0.5]) ranging from 1 to 30 μm, preferably from 5 to 25 μm, better still from 5 to 20 μm and even better still from 5 to 15 μm.

The hydrophobic silica aerogel particles may have a specific surface area per unit mass ($S_M$) ranging from 600 to 800 m$^2$/g and a size expressed as the volume mean diameter (D[0.5]) ranging from 5 to 20 μm and even better still from 5 to 15 μm. The hydrophobic silica aerogel particles may have a specific surface area per unit of volume Sv ranging from 5 to 60 m$^2$/cm$^3$, preferably from 10 to 50 m$^2$/cm$^3$ and better still from 15 to 40 m$^2$/cm$^3$.

Particularly useful aerogels include hydrophobic silica aerogels, preferably of silyl silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups. In some instances, it is particularly useful to use hydrophobic silica aerogel particles surface-modified with trimethylsilyl groups. Mention may be made of the aerogels sold by the company Cabot under the references DOWSIL VM-2270 by DOW, AEROGEL TLD 201, AEROGEL OGD 201, AEROGEL TLD 203, ENOVA AEROGEL MT 1100 and Enova AEROGEL MT 1200.

The total amount of optionally modified silicas in the cosmetic compositions, if present, may vary but is typically about 1 to about 20 wt. %, based on the total weigh of the cosmetic composition. The total amount of the optionally modified silicas may be about 1 to about 15 wt. %, about 1 t about 10 wt. %, about 1 to about 8 wt. %, about 1 to about 5 wt. %, about 2 to about 20 wt. %, about 2 to about 15 wt. %, about 2 to about 10 wt. %, about 2 to about 8 wt. %, about 2 to about 5 wt. %, about 3 to about 20 wt. %, about 3 to about 15 wt. %, about 3 to about 10 wt. %, about 3 to about 8 wt. %, or about 3 to about 5 wt. %, based on the total weight of the cosmetic composition.

ii) Optionally Modified Clays

Clays are silicates containing a cation that may be chosen from calcium, magnesium, aluminium, sodium, potassium and lithium cations, and mixtures thereof. Examples of such material include, but are not limited to clays of the smectite family, and also of the vermiculite, stevensite and chlorite families. These clays can be of natural or synthetic origin.

Mention may particularly be made of smectites, such as saponites, hectorites, montmorillonites, bentonites or beidellite and in particular synthetic hectorites (also known as laponites), such as the products sold by Rockwood Additives Limited under the names LAPONITE XLS, LAPONITE XLG, LAPONITE RD, LAPONITE RDS and LAPONITE XL21 (these products are sodium magnesium silicates and in particular sodium lithium magnesium silicates); bentonites, such as the product sold under the name BENTONE HC by Rheox; magnesium aluminium silicates, which are in particular hydrated, such as the products sold by Vanderbilt Company under the name VEEGUM ULTRA, VEEGUM HS or VEEGUM DGT, or also calcium silicates and in particular that in synthetic form sold by the company under the name MICRO-CEL C.

In some instances organophilic clays are preferred, more particularly modified clays, such as montmorillonite, bentonite, hectorite, attapulgite and sepiolite, and mixtures thereof. The clay is preferably an optionally modified bentonite or an optionally modified hectorite. Clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made of hectorites modified with a quaternary amine, more specifically with a $C_{10}$ to $C_{22}$ fatty acid ammonium halide, such as a chloride, such as hectorite modified with distearyldimethylammonium chloride (CTFA name: Disteardimonium hectorite), for instance the product sold under the name BENTONE 38V, BENTONE 38V CG or BENTONE EW CE by the company Elementis, or stearalkonium hectorites, such as BENTONE 27 V. In some instances, the clay is preferably disteardimonium hectorite.

Mention may also be made of quaternium-18 bentonites, such as those sold under the names BENTONE 34 by the company Elementis, TIXOGEL VP by the company United Catalyst and CLAYTONE 40 by the company Southern Clay; stearalkonium bentonites, such as those sold under the names TIXOGEL LG by the company United Catalyst and CLAYTONE AF and CLAYTONE APA by the company Southern Clay; or quaternium-18/benzalkonium bentonites, such as that sold under the name CLAYTONE HT by the company Southern Clay.

In some instances, it is preferable that the clay is chosen from organophilic modified clays, in particular organophilic modified hectorites, in particular modified with distearyldimethylammonium chloride (CTFA name: Disteardimonium hectorite).

The total amount of the optionally modified clays in the cosmetic compositions may vary but is typically about 1 to about 20 wt. %, based on the total weigh of the cosmetic composition. The total amount of the optionally modified clays may be about 1 to about 15 wt. %, about 1 t about 10 wt. %, about 1 to about 8 wt. %, about 1 to about 5 wt. %, about 2 to about 20 wt. %, about 2 to about 15 wt. %, about 2 to about 10 wt. %, about 2 to about 8 wt. %, about 2 to about 5 wt. %, about 3 to about 20 wt. %, about 3 to about 15 wt. %, about 3 to about 10 wt. %, about 3 to about 8 wt. %, or about 3 to about 5 wt. %, based on the total weight of the cosmetic composition.

Silicone Elastomers

The silicone elastomers can be non-emulsifying silicone elastomers, emulsifying silicone elastomers, or a mixture thereof. Non-emulsifying silicone elastomers include, but are not limited to, those organopolysiloxane elastomers not containing a hydrophilic chain, such as polyoxyalkylene or polyglycerolated chains. On the other hand, emulsifying silicone elastomers include, but are not limited to, polyoxyalkylenated silicone elastomers and a polyglycerolated silicone elastomers.

The total amount of silicone elastomers in the cosmetic compositions can vary but is typically about 1 to about 40 wt. %, based on the total weight of the cosmetic composition. In some cases, the total amount of silicone elastomers may be about 1 to about 35 wt. %, about 1 to about 30 wt. %, about 1 to about 25 wt. %, about 1 to about 20 wt. %, about 1 to about 15 wt. %, about 1 to about 10 wt. %, about 2 to about 40 wt. %, about 2 to about 35 wt. %, about 2 to about 30 wt. %, about 2 to about 25 wt. %, about 2 to about 20 wt. %, about 2 to about 15 wt. %, or about 2 to about 10 wt. %, based on the total weight of the cosmetic composition.

i. Non-Emulsifying Silicone Elastomers

The term "non-emulsifying" silicone elastomers defines organopolysiloxane elastomers not containing a hydrophilic chain, such as polyoxyalkylene or polyglycerolated chains.

Non-emulsifying silicone elastomers include elastomeric crosslinked organopolysiloxanes that can be obtained by a crosslinking addition reaction of diorganopolysiloxane containing at least one hydrogen bonded to silicon and of diorganopolysiloxane containing ethylenically unsaturated groups bonded to silicon, in particular in the presence of a platinum catalyst; or by a dehydrogenation crosslinking condensation reaction between a diorganopolysiloxane containing hydroxyl end groups and a diorganopolysiloxane containing at least one hydrogen bonded to silicon, in particular in the presence of an organotin; or by a crosslinking condensation reaction of a diorganopolysiloxane containing hydroxyl end groups and of a hydrolysable organopolysilane; or by thermal crosslinking of organopolysiloxane, in particular in the presence of an organoperoxide catalyst; or by crosslinking of organopolysiloxane via high-energy radiation such as gamma rays, ultraviolet rays or an electron beam.

A non-limiting example of a non-emulsifying silicone elastomer is dimethicone crosspolymer. In some instances, the non-emulsifying silicone elastomer is a cross-linked silicone, for example, dimethicone crosspolymer, (dimethicone/vinyl dimethicone) crosspolymer, (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and a mixture thereof. In some instances, dimethicone crosspolymer is particularly preferred.

In some instances, the elastomeric crosslinked organopolysiloxane is obtained by crosslinking addition reaction (A2) of diorganopolysiloxane containing at least two hydrogens each bonded to a silicon, and (B2) of diorganopolysiloxane containing at least two ethylenically unsaturated groups bonded to silicon, in particular in the presence (C2) of a platinum catalyst, as described, for example, in patent application EP295886, which is incorporated herein by reference in its entirety.

In some instances, the organopolysiloxane can be obtained by reaction of dimethylpolysiloxane containing dimethylvinylsiloxy end groups and of methylhydrogenopolysiloxane containing trimethylsiloxy end groups, in the presence of a platinum catalyst.

Compound (A2) is the base reactant for the formation of elastomeric organopolysiloxane, and the crosslinking is performed by an addition reaction of compound (A2) with compound (B2) in the presence of the catalyst (C2). Compound (A2) may be a diorganopolysiloxane containing at least two lower (for example $C_2$-$C_4$) alkenyl groups; the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane (A2) may have a branched-chain, linear-chain, cyclic or networked structure, but the linear-chain structure is preferred. Compound (A2) may have a viscosity ranging from the liquid state to the gum state. Preferably, compound (A2) has a viscosity of at least 100 centistokes at 25° C.

The organopolysiloxanes (A2) may be chosen from methylvinylsiloxanes, methylvinylsiloxane-dimethyl-siloxane copolymers, dimethylpolysiloxanes containing dimethylvinylsiloxy end groups, copolymers of dimethyl-siloxane-methylphenylsiloxane containing dimethylvinyl-siloxy end groups, copolymers of dimethylsiloxane-diphenylsiloxane-methylvinylsiloxane containing dimethylvinylsiloxy end groups, copolymers of dimethyl-siloxane-methylvinylsiloxane containing trimethylsiloxy end groups, copolymers of dimethylsiloxane-methyl-phenylsiloxane-methylvinylsiloxane containing trimethylsiloxy end groups, methyl(3,3,3-trifluoro-propyl)polysiloxanes containing dimethylvinylsiloxy end groups, and copolymers of dimethylsiloxane-methyl-(3,3,3-trifluoropropyl)siloxane containing dimethylvinylsiloxy end groups.

Compound (B2) is in particular an organopolysiloxane containing at least 2 hydrogens bonded to silicon in each molecule and is thus the crosslinking agent for compound (A2).

In some instances, the sum of the number of ethylenic groups per molecule of compound (A2) and the number of hydrogen atoms bonded to silicon per molecule of compound (B2) is at least 4.

Compound (B2) may be in any molecular structure, in particular of linear-chain or branched-chain structure, or cyclic structure. Compound (B2) may have a viscosity at 25° C. ranging from 1 to 50 000 centistokes, in particular so as to have good miscibility with compound (A). It is advantageous for compound (B2) to be added in an amount such that the molecular ratio between the total amount of hydrogen atoms bonded to silicon in compound (B2) and the total amount of all the ethylenically unsaturated groups in compound (A2) is within the range of from 1/1 to 20/1.

Compound (B2) may be chosen from methylhydrogenopolysiloxanes containing trimethylsiloxy end groups, copolymers of dimethylsiloxane-methylhydrogenosiloxane containing trimethylsiloxy end groups, and dimethyl-siloxane-methylhydrogenosiloxane cyclic copolymers.

Compound (C2) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black, or platinum on a support.

The catalyst (C2) is preferably added at from 0.1 to 1000 parts by weight, better still from 1 to 100 parts by weight, as clean platinum metal per 1000 parts by weight of the total amount of compounds (A2) and (B2).

Other organic groups may be bonded to silicon in the organopolysiloxanes (A2) and (B2) described above, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The non-emulsifying silicone elastomer according to the invention can be mixed with at least one hydrocarbon-based oil and/or one silicone oil so as to form a gel. In these gels, the non-emulsifying elastomer is often in the form of non-spherical particles.

Non-emulsifying elastomers that may be used include those sold under the names DOWSIL EL-8048 from DOW (INCI: Isododecane (and) Dimethicone Crosspolymer), KSG-6, KSG-15, KSG-16, KSG-18, KSG-41, KSG-42, KSG-43, KSG-44, USG-105 and USG-106 by the company Shin-Etsu, DC9040, DC9041, DC9509, DC9505, DC9506, DC5930, DC9350, DC9045 and DC9043 by the company Dow Corning, Gransil by the company Grant Industries, and SFE 839 by the company General Electric.

The total amount of non-emulsifying silicone elastomers in the cosmetic compositions, if present, may vary but is typically about 0.1 to about 20 wt. %, based on the total weight of the cosmetic composition. In some cases, the total amount of non-emulsifying silicone elastomers in the cosmetic compositions is about 0.1 to about 15 wt. %, about 0.1 to about 10 wt. %, about 0.1 to about 5 wt. %, about 1 to about 20 wt. %, about 1 to about 15 wt. %, about 1 to about 10 wt. %, or about 1 to about 5 wt. %, based on the total weight of the cosmetic composition.

ii. Emulsifying Silicone Elastomers

The term "emulsifying silicone elastomer" is intended to mean a silicone elastomer comprising at least one hydrophilic chain. For example, emulsifying silicone elastomers may be chosen from polyoxyalkylenated silicone elastomers, polyglycerolated silicone elastomers, and a mixture thereof.

a. Polyoxyalkylenated Silicone Elastomers: A polyoxyalkylenated silicone elastomer may be a crosslinked organopolysiloxane that can be obtained by crosslinking addition reaction of diorganopolysiloxane containing at least one hydrogen bonded to silicon and of a polyoxyalkylene having at least two ethylenically unsaturated groups. In particular, the polyoxyalkylenated crosslinked organopolysiloxane may be obtained by crosslinking addition reaction (A1) of diorganopolysiloxane containing at least two hydrogens each bonded to a silicon, and (B1) of polyoxyalkylene containing at least two ethylenically unsaturated groups, in particular in the presence (C1) of a platinum catalyst, as described, for example, in U.S. Pat. Nos. 5,236,986 and 5,412,004, which are incorporated herein by reference in their entirety.

The organopolysiloxane can be obtained by reaction of polyoxyalkylene (in particular polyoxyethylene and/or polyoxypropylene) containing dimethylvinylsiloxy end groups and of methylhydrogeno-polysiloxane containing trimethylsiloxy end groups, in the presence of a platinum catalyst.

The organic groups bonded to silicon atoms of the compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenyl-ethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may be chosen from methylhydrogenopolysiloxanes containing trimethylsiloxy end groups, copolymers of dimethylsiloxane-methylhydrogenosiloxane containing trimethylsiloxy end groups, cyclic dimethylsiloxane-methylhydrogenosiloxane copolymers, and copolymers of dimethylsiloxane-methylhydrogenosiloxane-laurylmethylsiloxane containing trimethylsiloxy end groups.

Compound (C1) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black and platinum on a support.

In some cases, the polyoxyalkylenated silicone elastomers may be formed from divinyl compounds, in particular polyoxyalkylenes having at least two vinyl groups, reacting with Si—H bonds of a polysiloxane.

The polyoxyalkylenated silicone elastomers are often mixed with at least one hydrocarbon-based oil and/or one silicone oil so as to form a gel. In these gels, the polyoxyalkylenated elastomer can be in the form of non-spherical particles. Polyoxyalkylenated elastomers are in particular described in U.S. Pat. Nos. 5,236,986, 5,412,004, 5,837,793 and 5,811,487, which are incorporated herein by reference in their entirety. Further, useful polyoxyalkylenated silicone elastomers include, but are not limited to, those sold under the names KSG-21, KSG-20, KSG-30, KSG-31, KSG-32, KSG-33, KSG-210, KSG-310, KSG-320, KSG-330, KSG-340 and X-226146 by the company Shin-Etsu, and DC9010 and DC9011 by the company Dow Corning.

b. Polyglycerolated Silicone Elastomers: Polyglycerolated silicone elastomers are typically crosslinked elastomeric organopolysiloxanes that can be obtained by a crosslinking addition reaction of diorganopolysiloxane containing at least one hydrogen bonded to silicon and of polyglycerolated compounds having ethylenically unsaturated groups, often carried out in the presence of a platinum catalyst. For instance, in some cases, the crosslinked elastomeric organopolysiloxane is obtained by crosslinking addition reaction (A) of diorganopolysiloxane containing at least two hydrogens each bonded to a silicon, and (B) of glycerolated compounds having at least two ethylenically unsaturated groups, in particular in the presence (C) of a platinum catalyst. In some instances, the organopolysiloxane can be obtained by reaction of a polyglycerolated compound containing dimethylvinylsiloxy end groups and of methylhydrogenopolysiloxane containing trimethylsiloxy end groups, in the presence of a platinum catalyst.

Compound (A) is the base reactant for the formation of elastomeric organopolysiloxane and the crosslinking is performed by an addition reaction of compound (A) with compound (B) in the presence of the catalyst (C). Compound (A) may be, for example, an organopolysiloxane containing at least 2 hydrogen atoms bonded to different silicon atoms in each molecule. Compound (A) may have any molecular structure, in particular a linear chain or branched chain structure or a cyclic structure. Furthermore, compound (A) may have a viscosity at 25° C. ranging from 1 to 50,000 centistokes, in particular so as to have good miscibility with compound (B).

The organic groups bonded to the silicon atoms of compound (A) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. In some instances, it is preferable that said organic group is chosen from methyl, phenyl and lauryl groups.

Compound (A) can thus be chosen from methylhydrogenopolysiloxanes containing trimethylsiloxy end groups, copolymers of dimethylsiloxane-methyl-hydrogenosiloxane containing trimethylsiloxy end groups, dimethylsiloxane-methylhydrogenosiloxane cyclic copolymers, and copolymers of dimethylsiloxane-methyl-hydrogenosiloxane-laurylmethylsiloxane containing trimethylsiloxy end groups.

Compound (B) may be a polyglycerolated compound corresponding to formula (B') below:

$$C_mH_{2m-1}\text{—O—}[Gly]_n\text{-}CmH_{2m-1} \qquad (B')$$

in which m is an integer ranging from 2 to 6, n is an integer ranging from 2 to 200, preferably ranging from 2 to 100, preferably ranging from 2 to 50, preferably n ranging from 2 to 20, preferably from 2 to 10, and preferentially ranging from 2 to 5, and in particular equal to 3; Gly denotes:

—CH$_2$—CH(OH)—CH$_2$—O— or —CH$_2$—CH(CH$_2$OH)—O—

Often, the sum of the number of ethylenic groups per molecule of compound (B) and of the number of hydrogen atoms bonded to silicon atoms per molecule of compound (A) is at least 4.

It can be advantageous for compound (A) to be added in an amount such that the molecular ratio between the total amount of hydrogen atoms bonded to silicon atoms in compound (A) and the total amount of all the ethylenically unsaturated groups in compound (B) is within the range of from 1/1 to 20/1.

Compound (C) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black, or platinum on a support. The catalyst (C) is preferably added at from 0.1 to 1000 parts by weight, better still from 1 to 100 parts by weight, as clean platinum metal per 1000 parts by weight of the total amount of compounds (A) and (B).

The polyglycerolated silicone elastomers are often mixed with at least one hydrocarbon-based oil and/or one silicone oil so as to form a gel. In these gels, the polyglycerolated elastomer is often in the form of non-spherical particles. Such elastomers are in particular described in patent application WO 2004/024798, which is incorporated herein by reference in its entirety. As polyglycerolated silicone elastomers, mention may be made of those sold under the names KSG-710, KSG-810, KSG-820, KSG-830 and KSG-840 by the company Shin-Etsu.

The total amount of emulsifying silicone elastomers in the cosmetic compositions, if present, may vary but is typically about 0.1 to about 20 wt. %, based on the total weight of the cosmetic composition. In some cases, the total amount of emulsifying silicone elastomers in the cosmetic compositions is about 0.1 to about 15 wt. %, about 0.1 to about 10 wt. %, about 0.1 to about 5 wt. %, about 1 to about 20 wt. %, about 1 to about 15 wt. %, about 1 to about 10 wt. %, or about 1 to about 5 wt. %, based on the total weight of the cosmetic composition.

Hydrophobic Film Forming Polymers

The term "hydrophobic film-forming polymer" denotes a film-forming polymer that has no or limited affinity for water and, in this respect, does not lend itself to a formulation in the form of a solute in an aqueous medium. In particular, the term "hydrophobic polymer" means a polymer having a solubility in water at 25° C. of less than 1% by weight.

The term "film-forming polymer" means a polymer that is capable of forming, by itself or in the presence of an auxiliary film-forming agent, a macroscopically continuous deposit on a support, especially on keratin materials, and preferably a cohesive deposit, and better still a deposit whose cohesion and mechanical properties are such that said deposit may be isolable and manipulable in isolation, for example when said deposit is prepared by pouring onto a non-stick surface, for instance a Teflon-coated or silicone-coated surface.

Hydrophobic film-forming polymers may be a polymer chosen from:
film-forming polymers that are soluble in an organic solvent medium, in particular liposoluble polymers; this means that the polymer is soluble or miscible in the organic medium and forms a single homogeneous phase when it is incorporated into the medium; and
film-forming polymers that are dispersible in an organic solvent medium, which means that the polymer forms an insoluble phase in the organic medium, the polymer remaining stable and/or compatible once incorporated into this medium. In particular, such polymers may be in the form of non-aqueous dispersions of polymer particles, preferably dispersions in silicone oils or hydrocarbon-based oils; in one embodiment, the non-aqueous polymer dispersions comprise polymer particles stabilized on their surface with at least one stabilizer; these non-aqueous dispersions are often referred to as NADs.

Hydrophobic film-forming polymers that may be mentioned include homopolymers and copolymers of a compound bearing an ethylenic unit, acrylic polymers and copolymers, polyurethanes, polyesters, silicone polymers such as polymers bearing a non-silicone organic backbone grafted with monomers containing a polysiloxane, and polyisoprenes.

In some instances, useful hydrophobic film-forming polymers include lipodispersible film-forming polymers in the form of non-aqueous dispersions of polymer particles, block ethylenic copolymers, vinyl polymers comprising at least one carbosiloxane dendrimer-based unit, silicone acrylate copolymers and mixtures thereof, preferably lipodispersible film-forming polymers in the form of non-aqueous dispersions of polymer particles (NADs).

i. Lipodispersible Film-Forming Polymers in the Form of Non-Aqueous Dispersions of Polymer Particles, Also Known as NADs Non-aqueous dispersions of hydrophobic film-forming polymer that may be used include dispersions of particles of a grafted ethylenic polymer, preferably an acrylic polymer, in a liquid oily phase for example, in the form of surface-stabilized particles dispersed in the liquid fatty phase. The dispersion of surface-stabilized polymer particles may be manufactured as described in document WO 04/055081, which is incorporated herein by reference in its entirety.

ii. Block Ethylenic Copolymer

The hydrophobic film-forming polymer may be a block ethylenic copolymer, containing at least a first block with a glass transition temperature ($T_g$) of greater than or equal to 40° C. and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., said first block and said second block being connected together via a statistical intermediate segment comprising at least one of said first constituent monomers of the first block and at least one of said second constituent monomers of the second block, and said block copolymer having a polydispersity index I of greater than 2. Polymers of this type that are suitable for use in the invention are described in document EP 1 411 069, which is incorporated herein by reference in its entirety. A non-limiting examples includes the product MEXOMER PAS (acrylic acid/isobutyl acrylate/isobornyl acrylate copolymer diluted to 50% in isododecane) sold by the company Chimex.

iii. Vinyl Polymer Comprising at Least One Carbosiloxane Dendrimer-Based Unit

The hydrophobic film-forming polymer may be at least one vinyl polymer comprising at least one carbosiloxane dendrimer-based unit. The vinyl polymer typically has a backbone and at least one side chain, which comprises a carbosiloxane dendrimer-based unit having a carbosiloxane dendrimer structure. Vinyl polymers comprising at least one carbosiloxane dendrimer unit as described in applications WO 03/045 337 and EP 963 751, which are incorporated herein by reference in their entirety.

The term "carbosiloxane dendrimer structure" is a molecular structure with branched groups of high molecular masses, said structure having high regularity in the radial direction starting from the bond to the backbone. Such carbosiloxane dendrimer structures are described in the form of a highly branched siloxane-silylalkylene copolymer in the laid-open Japanese patent application Kokai 9-171 154, which is incorporated herein by reference in their entirety.

A vinyl polymer bearing at least one carbosiloxane dendrimer-based unit has a molecular side chain containing a carbosiloxane dendrimer structure, and may be derived from the polymerization of:

(A) from 0 to 99.9 parts by weight of a vinyl monomer; and (B) from 100 to 0.1 part by weight of a carbosiloxane dendrimer containing a radical-polymerizable organic group, represented by the general formula:

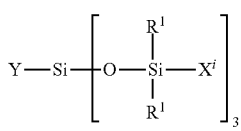

in which Y represents a radical-polymerizable organic group, R.sup.1 represents an aryl group or an alkyl group containing from 1 to 10 carbon atoms, and $X^i$ represents a silylalkyl group which, when i=1, is represented by the formula:

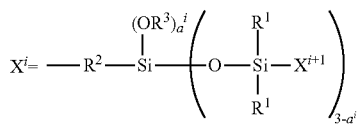

in which R.sup.1 is as defined above, R.sup.2 represents an alkylene group containing from 2 to 10 carbon atoms, R.sup.3 represents an alkyl group containing from 1 to 10 carbon atoms, X.sup.i+1 represents a hydrogen atom, an alkyl group containing from 1 to 10 carbon atoms, an aryl group, or the silylalkyl group defined above with i=i+1; i is an integer from 1 to 10 which represents the generation of said silylalkyl group, and a' is an integer from 0 to 3;

in which said radical-polymerizable organic group contained in the component (A) is chosen from:

organic groups containing a methacrylic group or an acrylic group and that are represented by the formulae:

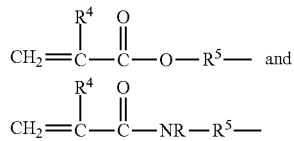

in which $R^4$ represents a hydrogen atom or an alkyl group, $R^5$ represents an alkylene group containing from 1 to 10 carbon atoms; and organic groups containing a styryl group and that are represented by the formula:

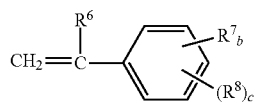

in which $R^6$ represents a hydrogen atom or an alkyl group, $R^7$ represents an alkyl group containing from 1 to 10 carbon atoms, $R^8$ represents an alkylene group containing from 1 to 10 carbon atoms, b is an integer from 0 to 4, and c is 0 or 1, such that if c is 0, —$(R^8)_c$— represents a bond.

The monomer of vinyl type that is the component (A) in the vinyl polymer is a monomer of vinyl type that contains a radical-polymerizable vinyl group.

The following are examples of this monomer of vinyl type: methyl methacrylate, ethyl methacrylate, n-propyl methacrylate, isopropyl methacrylate or a methacrylate of an analogous lower alkyl; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or a higher-analogue methacrylate; vinyl acetate, vinyl propionate or a vinyl ester of an analogous lower fatty acid; vinyl caproate, vinyl 2-ethylhexoate, vinyl laurate, vinyl stearate or an ester of an analogous higher fatty acid; styrene, vinyltoluene, benzyl methacrylate, phenoxyethyl methacrylate, vinylpyrrolidone or similar vinylaromatic monomers; methacrylamide, N-methylolmethacrylamide, N-methoxymethyl-methacrylamide, isobutoxymethoxymethacrylamide, N,N-dimethylmethacrylamide or similar monomers of vinyl type containing amide groups; hydroxyethyl methacrylate, hydroxypropyl alcohol methacrylate or similar monomers of vinyl type containing hydroxyl groups; acrylic acid, methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or a similar monomer of vinyl type with ether bonds; methacryloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional monomers of vinyl type may also be used.

The following are examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropane trioxyethylmethacrylate, tris(2-hydroxyethyl) isocyanurate dimethacrylate, tris(2-hydroxyethyl) isocyanurate trimethacrylate, polydimethylsiloxane capped with styryl groups bearing divinylbenzene groups on the two ends, or similar silicone compounds bearing unsaturated groups.

To facilitate the preparation of starting material mixture for cosmetic products, the number-average molecular mass of the vinyl polymer bearing a carbosiloxane dendrimer may be chosen within the range between 3000 g/mol and 2,000,000 g/mol and preferably between 5000 g/mol and 800,000 g/mol. It may be a liquid, a gum, a paste, a solid, a powder, or any other form. The preferred forms are solutions consisting of the dilution of a dispersion or of a powder in solvents such as a silicone oil or an organic oil.

According to one preferred embodiment, a vinyl polymer grafted in the sense of the present invention may be conveyed in an oil or a mixture of oils, which is/are preferably volatile, chosen in particular from silicone oils and hydrocarbon-based oils, and mixtures thereof. A non-limiting silicone oil that is suitable for use is cyclopentasiloxane. Similarly, a non-limiting hydrocarbon-based oil that is suitable for use is isododecane.

Vinyl polymers grafted with at least one carbosiloxane dendrimer-based unit include the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning.

In some instances, the vinyl polymer grafted with at least one carbosiloxane dendrimer-based unit is an acrylate/polytrimethyl siloxymethacrylate copolymer, for example, the product sold in isododecane under the name Dow Corning FA 4002 ID Silicone Acrylate.

iv. Silicone Acrylate Copolymers

In some instances, one or more of the hydrophobic film-forming polymers include at least one copolymer comprising carboxylate groups and polydimethylsiloxane groups. The term "copolymer comprising carboxylate groups and polydimethylsiloxane groups" means a copolymer obtained from (a) one or more carboxylic (acid or ester) monomers, and (b) one or more polydimethylsiloxane (PDMS) chains. The term "carboxylic monomer" means both carboxylic acid monomers and carboxylic acid ester monomers.

The monomer (a) may be chosen, for example, from acrylic acid, methacrylic acid, maleic acid, fumaric acid, itaconic acid, crotonic acid, esters thereof and mixtures of these monomers. Esters that may be mentioned include the following monomers: acrylate, methacrylate, maleate, fumarate, itaconate and/or crotonate. According to one preferred embodiment of the invention, the monomers in ester form are more particularly chosen from linear or branched, preferably $C_1$-$C_{24}$ and better still $C_1$-$C_{22}$ alkyl acrylates and methacrylates, the alkyl radical preferably being chosen from methyl, ethyl, stearyl, butyl and 2-ethylhexyl radicals, and mixtures thereof. Thus, in some instances, the copolymer comprises as carboxylate groups at least one group chosen from acrylic acid and methacrylic acid, and methyl, ethyl, stearyl, butyl or 2-ethylhexyl acrylate or methacrylate, and mixtures thereof.

The term "polydimethylsiloxanes" (also known as organopolysiloxanes and abbreviated as PDMS) denotes any organosilicon polymer or oligomer of linear structure, of variable molecular weight, obtained by polymerization and/or polycondensation of suitably functionalized silanes, and consisting essentially of a repetition of main units in which the silicon atoms are linked together via oxygen atoms (siloxane bond ≡Si—O—Si≡), comprising trimethyl radicals directly linked via a carbon atom to said silicon atoms. The PDMS chains that may be used to obtain the copolymer used according to the invention comprise at least one polymerizable radical group, preferably located on at least one of the ends of the chain, i.e. the PDMS may contain, for example, a polymerizable radical group on the two ends of the chain or one polymerizable radical group on one end of the chain and one trimethylsilyl end group on the other end of the chain. The polymerizable radical group may especially be an acrylic or methacrylic group, in particular a group $CH_2$=$CR_1$—CO—O—$R_2$, in which $R_1$ represents a hydrogen or a methyl group and $R_2$ represents —$CH_2$—, —$(CH_2)_n$— with n=3, 5, 8 or 10, —$CH_2$—$CH(CH_3)$—$CH_2$—, —$CH_2$—$CH_2$—O—$CH_2$—$CH_2$—, —$CH_2$—$CH_2$—O—$CH_2$—$CH_2$—$CH(CH_3)$—$CH_2$—, —$CH_2$—$CH_2$—O—$CH_2$—$CH_2$—, or —$CH_2$—O—$CH_2$—$CH_2$—$CH_2$—.

The copolymers are generally obtained according to the usual methods of polymerization and grafting, for example by free-radical polymerization (A) of a PDMS comprising at least one polymerizable radical group (for example on one of the ends of the chain or on both ends) and (B) of at least one carboxylic monomer. The copolymers obtained may have a molecular weight ranging from about 3000 g/mol to 200 000 g/mol and preferably from about 5000 g/mol to 100 000 g/mol. The copolymer may be in its native form or in dispersed form in a solvent such as lower alcohols containing from 2 to 8 carbon atoms, for instance isopropyl alcohol, or oils, for instance volatile silicone oils (for example cyclopentasiloxane).

As copolymers that may be used, mention may be made, for example, of copolymers of acrylic acid and of stearyl acrylate containing polydimethylsiloxane grafts, copolymers of stearyl methacrylate containing polydimethylsiloxane grafts, copolymers of acrylic acid and of stearyl methacrylate containing polydimethylsiloxane grafts, copolymers of methyl methacrylate, butyl methacrylate, 2-ethylhexyl acrylate and stearyl methacrylate containing polydimethylsiloxane grafts. As copolymers that may be used, mention may be made in particular of the copolymers sold by the company Shin-Etsu under the names KP-561 (CTFA name: acrylates/dimethicone), KP-541 in which the copolymer is dispersed at 60% by weight in isopropyl alcohol (CTFA name: acrylates/dimethicone and isopropyl alcohol), and KP-545 in which the copolymer is dispersed at 30% in cyclopentasiloxane (CTFA name: acrylates/dimethicone and cyclopentasiloxane). Mention may also be made of the grafted copolymer of polyacrylic acid and dimethylpolysiloxane dissolved in isododecane, sold by the company Shin-Etsu under the name KP-550.

The total amount of hydrophobic film forming polymers in the cosmetic compositions can vary but is typically at least 5 wt. %, based on the total weight of the cosmetic composition. More specifically, the total amount of hydrophobic film forming polymers may be at least 5 wt. % to about 40 wt. %, at least 5 wt. % to about 30 wt. %, at least 5 wt. % to about 25 wt. %, based on the total weight of the cosmetic composition. Furthermore, the total amount of hydrophobic film forming polymers may be about 5 wt. % to about 30 wt. %, about 5 wt. % to about 25 wt. %, about 5 wt. %, to about 20 wt. %, about 5 wt. % to about 15 wt. %, about 6 wt. % to about 30 wt. %, about 6 wt. % to about 25 wt. %, about 6 wt. % to about 20 wt. %, about 6 wt. % to about 15 wt. %, or about 7 wt. % to about 14 wt. %, based on the total weight of the cosmetic composition.

Non-Volatile Fatty Substances

In addition to the volatile hydrocarbon oils mentioned above, the cosmetic compositions may optionally include one or more non-volatile fatty substances, in particular, non-volatile oils and waxes. Non-limiting examples of non-volatile oils include:

i. hydrocarbon oils of animal origin such as perhydrosqualene;
ii. plant hydrocarbon oils, such as liquid triglycerides of fatty acids, for example sunflower oil, corn oil, soybean oil, marrow oil, grapeseed oil, sesame oil, hazelnut oil, apricot oil, macadamia oil, castor oil, avocado oil, caprylic/capric acid triglycerides;
iii. oils of formula $R_9COOR_{10}$ in which $R_9$ represents a higher fatty acid residue containing from 7 to 19 carbon atoms and $R_{10}$ represents a branched hydrocarbon chain containing from 3 to 20 carbon atoms, such as, for example, Purcellin oil;
iv. linear or branched hydrocarbons of mineral or synthetic origin, such as non-volatile liquid paraffins and derivatives thereof, petroleum jelly (petrolatum), polydecenes, and hydrogenated polyisobutene such as parleam;

v. synthetic esters and ethers such as isopropyl myristate, octanoates, decanoates or ricinoleates of alcohols or of polyalcohols;

vi. fatty alcohols such as octyidodecanol or oleyl alcohol;

vii. partially hydrocarbonated and/or siliconated fluoro oils;

viii. silicone oils such as linear, non-volatile polydimethylsiloxanes (dimethicone) which are liquid or pasty at room temperature, phenyldimethicones, phenyltrimethicones and polymethylphenylsiloxanes; and mixtures thereof.

In some instances, the one or more fatty substances may be selected form polyolefins (petrolatum), waxes, squalane, squalene, hydrogenated polyisobutene, hydrogenated polydecene, polybutene, mineral oil, pentahydrosqualene, dimethicone, and a mixture thereof.

The total amount of the one or more non-volatile fatty substances, if present, may vary but is typically about 0.1 to about 30 wt. %, based on the total weight of the cosmetic compositions. The total amount of the one or more non-volatile fatty substances may be about 0.1 to about 25 wt. %, about 0.1 to about 20 wt. %, about 0.1 to about 15 wt. %, about 0.1 to about 10 wt. %, about 1 to about 30 wt. %, about 1 to about 25 wt. %, about 1 to about 20 wt. %, about 1 to about 15 wt. %, or about 1 to about 10 wt. %, based on the total weight of the cosmetic composition.

Inorganic Pigments

The cosmetic compositions may optionally include one or more inorganic pigments. Non-limiting examples include titanium dioxide, zirconium oxide, cerium oxide, zinc oxide, iron oxide, alumina, aluminum hydroxide, chromium oxide, manganese violet, ultramarine blue, chromium hydrate, ferric blue, aluminum powder, copper powder, silver powder, gold powder, barium sulfate, carbon black, and mixtures thereof.

The total amount of inorganic pigments, if present, may vary but is typically about 0.01 to about 10 wt. %, based on the total weigh of the cosmetic composition. The total amount of inorganic pigments may be about 0.01 to about 8 wt. %, about 0.01 to about 5 wt. %, about 0.01 to about 4 wt. %, about 0.1 to about 10 wt. %, about 0.1 to about 8 wt. %, about 0.1 to about 5 wt. %, or about 0.1 to about 4 wt. %, based on the total weight of the cosmetic composition.

Organic Colorants

The cosmetic compositions may optionally include one or more organic colorants. Non-limiting examples include D & C red no. 19 (CI 45,170), D & C red no. 9 (CI 15,585), D & C red no. 21 (CI 45,380), D & C orange no. 4 (CI 15,510), D & C orange no. 5 (CI 45,370), D & C red no. 27 (CI 45,410), D & C red no. 13 (CI 15,630), D & C red no. 7 (CI 15,850:1), D & C red no. 6 (CI 15,850:2), D & C yellow no. 5 (CI 19,140), D & C red no. 36 (CI 12,085), D & C orange no. 10 (CI 45,425), D & C yellow no. 6 (CI 15,985), D & C red no. 30 (CI 73,360), D & C red no. 3 (CI 45,430), carbon black (CI 77,266), cochineal carmine lake (CI 75,470), natural or synthetic melanin, and aluminium lakes.

The total amount of organic colorants, if present, may vary but is typically about 0.01 to about 10 wt. %, based on the total weigh of the cosmetic composition. The total amount of organic colourants may be about 0.01 to about 8 wt. %, about 0.01 to about 5 wt. %, about 0.01 to about 4 wt. %, about 0.1 to about 10 wt. %, about 0.1 to about 8 wt. %, about 0.1 to about 5 wt. %, or about 0.1 to about 4 wt. %, based on the total weight of the cosmetic composition.

Soft Focus Powder

The cosmetic compositions may optionally include soft focus powder. Soft focus powders are materials providing a blurring effect, typically due to their light-scattering properties on the skin. Such powders typically have high diffuse reflectance, low specular reflectance, and high diffuse transmittance. Soft focus powders give the skin a smoother appearance, for example, by reducing the difference in luminosity between the valley and the edges of wrinkles and imperfections.

Non-limiting examples of soft focus powders include powders of natural or synthetic origin such as mica, titanated mica, alumina, titanium dioxide, serecite, composite talc/titanium dioxide/alumina/silica powders, polyamide, poly (methyl (meth)acrylate), polyethylene powder, polymethylsilsesquioxane powder, sodium acrylates crosspolymer-2 and a mixture thereof. Additional non-limiting examples include calcium aluminum borosilicate (LUXSIL), PMMA (Microsphere M-100), polyethylene (POLYETHYLENE CI 2080), methyl methacrylate crosspolymer (COVABEADS LH85), nylon-12 (ORGASOL 2002), or ethylene/acrylic acid copolymer (FLOBEADS EA209). In some instances, the cosmetic compositions include at least one soft focus powder selected from the group consisting of silica which may or may not be coated, fumed silica, silica silylate, composite talc/titanium dioxide/alumina/silica powders, polyamide (nylon), poly(methyl (meth)acrylate), polyethylene powder, polymethylsilsesquioxane powder, waxes, such as copernicia cerifera (carnauba) wax, dimethicone/vinyl dimethicone crosspolymer, nylon-12, cellulose, polylactic acid, boron nitride, and a mixture thereof. The copernicia cerifera (carnauba) wax can be provided as a dispersion non water and alcohol. The dimethicone/vinyl dimethicone crosspolymer can be provided as silicone dispersion (INCI: Dimethicone/vinyl dimethicone crosspolymer (and) C12-14 Pareth-12). In some instances, the soft focus powder is (or includes) sodium acrylates crosspolymer-2, which is commercially available as AQUAKEEP 10SH-NFC as sodium acrylates crosspolymer-2 (and) water (and) silica.

The total amount of soft focus powder, if present, can vary but is typically about 0.1 to about 20 wt. %, based on the total weight of the cosmetic composition. In some cases, the total amount of soft focus powder is about 0.1 to about 15 wt. %, about 0.1 to about 10 wt. %, about 0.1 to about 5 wt. %, about 1 to about 20 wt. %, about 1 to about 15 wt. %, about 1 to about 10 wt. %, or about 1 to about 10 wt. %, based on the total weight of cosmetic composition.

Water-Soluble Solvents

The cosmetic composition may optionally include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvent has a solubility of at least 60%, 70%, 80%, or 90%. Non-limiting examples of water-soluble solvents include, for example, glycerin, $C_{1-4}$ alcohols, organic solvents, fatty alcohols, fatty ethers, fatty esters, polyols, glycols, and any a mixture thereof. In some instances, the cosmetic composition includes one or more $C_{1-4}$ alcohols, for example, ethanol.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the water-soluble solvents in the cosmetic composition, if present, may vary but is typically about 0.01 to about 25 wt. %, based on the total weight of the cosmetic composition. In some cases, the total amount of water-soluble solvents is about 0.01 to about 20 wt. %, about 0.01 to about 15 wt. %, about 0.01 to about 10 "dextrin palmitate" wt. %, about 0.1 to about 25 wt. %, about 0.1 to about 20 wt. %, about 0.1 to about 15 wt. %, about 0.1 to about 10 wt. %, about 1 to about 25 wt. %, about 1 to about 20 wt. %, "dextrin palmitate" about 1 to about 15 wt. %, about 1 to about 10 wt. %, or about 1 to about 8 wt. %, based on the total weight of the cosmetic composition.

Non-Mineral Thickening Agents

The cosmetic compositions may optionally include one or more non-mineral thickening agents. The non-mineral thickening agents may be lipophilic or hydrophilic, i.e., they may be appropriate for thickening an oily phase or an anhydrous composition or they may be appropriate for thickening an aqueous phase or an aqueous composition. For anhydrous compositions, lipophilic thickening agents or thickening agents that thicken anhydrous (e.g., oily) compositions are useful. Similarly, for aqueous compositions, hydrophilic thickening agents are useful.

Non-limiting examples of non-mineral thickening agents useful for thickening anhydrous compositions include C12-22 alkyl acrylate/hydroxyethylacrylate copolymer (IN-TELIMER), ethylene diamine/stearyl dimer dilinoleate copolymer such as OLEOCRAFT LP-10-PA-(MV) sold by Croda, polyamide-8 such as OLEOCRAFT LP-20-PA-(MV) sold by Croda, poly $C_{10}$-$C_{30}$ alkyl acrylate such as INTELIMER IPA 13-6 or INTELIMER IPA 13-1 NG Polymer sold by Air Products & Chemicals, and nylon-611/dimethicone copolymer such as Dow Corning 2-8179 Gellant sold by Dow Corning, dextrin palmitate such as RHEOPEARL KL2-OR sold by Chiba Flour Milling. Additional non-limiting examples of non-mineral thickening agents useful for thickening anhydrous compositions include thickening polymers such block copolymers of styrene with ethylene propylene and/or butylene available under the trade name KRATON, and particularly styrene ethylene/butylene styrene linear block copolymers. A related category of thickening polymer comprises polymers of alpha methylstyrene and styrene, such as those under the trade name KRISTALEX. Yet another thickening polymer comprises alkyl substituted galactomannan available under the trade name N-HANCE AG. Non-mineral thickening agents useful for thickening anhydrous compositions may also include thickening polymers such as vinyl pyrrolidone with polyethylene containing at least 25 methylene units, such as triacontanyl polyvinylpyrrolidone, under the trade name Antaron WP-660.

Non-limiting examples of thickening agents useful for thickening aqueous compositions include xanthan gum, guar gum, biosaccharide gum, cellulose, acacia Seneca gum, *sclerotium* gum, agarose, pechtin, gellan gum, hyaluronic acid. Additionally, the one or more non-mineral thickening agents may be polymeric thickeners such as, for example, ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer, and sodium acrylates crosspolymer-2, which is commercially available as AQUAKEEP 10SH-NFC as sodium acrylates crosspolymer-2 (and) water (and) silica.

Additional, non-limiting examples of various types of non-mineral thickening agents include:

i. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol.RTM. 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol.

These copolymers are known as acrylates/C10-C30 alkyl acrylate crosspolymers and are commercially available as Carbopol.RTM. 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

ii. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228,868, which are all incorporated herein by reference in their entirety.

iii. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

iv. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

v. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

The total amount of non-mineral thickening agent in the cosmetic compositions, if present, may vary. If present, the total amount of non-mineral thickening agents may be about 0.01 to about 15 wt. %, based on the total weight of the cosmetic composition. In some instances, the total amount of the non-mineral thickening agents may be about 0.01 to about 10 wt. %, about 0.01 to about 5 wt. %, about 0.1 to about 15 wt. %, about 0.1 to about 10 wt. %, or about 0.1 to about 5 wt. %, based on the total weight of the cosmetic composition.

Methods

The cosmetic compositions are particularly useful for improving the appearance of skin, especially the skin of a human. When the cosmetic compositions are applied to the skin, they provide an immediate improvement to the appearance of the skin that is long lasting. The cosmetic compositions are particularly useful for method of:

reducing the appearance of fine lines of the skin;
reducing the appearance of wrinkles of the skin;
improving the tone of skin and/or improving the evenness of skin tone;
improving skin softness and/or smoothness;
reducing the appearance of eye bags;
reducing the appearance of dark circles around and/or below the eyes;
reducing the appearance of pores and/or scars; and/or
increasing the radiance, luminosity, and/or glow of the skin.

Typically, an effective amount of a cosmetic composition is applied to the skin to be treated, for example, the skin of the face and/or neck. In some instances, it may be desirable to apply the cosmetic composition to the skin around (or below) the eyes. The cosmetic compositions can be applied with the hands or may be applies using a brush, sponge, tissue, cotton swab, fabric, or applicator (e.g., pen or other device), etc. The amount needed to achieve the desired effect can be ascertain by the consumer.

EMBODIMENTS

In one embodiment, cosmetic compositions according to the instant disclosure include:
  about 30 to about 85 wt. %, preferably about 35 to about 80 wt. %, more preferably about 40 to about 75 wt. % of one or more volatile hydrocarbon oils, preferably, one or more volatile hydrocarbon oils are selected from branched C8 to C16 alkanes, such as, for example, isoparaffin, isohexadecane, isododecane, isodecane, undecane, tridecane, dodecane, and a mixture thereof;
  about 1 to about 20 wt. %, preferably about 1 to about 15 wt. %, more preferably about 1 to about 10 wt. % of one or more mineral thickening agents, preferably one or more optionally modified silicas and/or one or more optionally modified clays, in particular, hydrophobic silica aerogels (e.g., silica silylate) and/or organophilic modified clays (e.g., organophilic modified hectorites such as disteardimonium hectorite);
  about 1 to about 40 wt. %, preferably about 1 to about 30 wt. %, more preferably about 5 to about 25 wt. % of one or more silicone elastomers, which may be emulsifying or non-emulsifying, in particular, at least one non-emulsifying silicone elastomer such as a cross-linked silicone selected from dimethicone crosspolymer, (dimethicone/vinyl dimethicone) crosspolymer, (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and a mixture thereof; and
  at least 5 wt. %, preferably at least 5 wt. % to about 30 wt. %, more preferably about 6 wt. % to about 25 wt. % of one or more hydrophobic film forming polymers, for instance block ethylenic copolymers, vinyl polymers comprising at least one carbosilxane dendrimer, based unit, silicone acrylate copolymers, and a mixture thereof;
    wherein the weight ratio of the total amount of hydrophobic film forming polymers to the total amount of mineral thickening agent (film forming polymers: mineral thickening agent) is about 1:1 to about 8:1, preferably about 1.1:1 to about 7:1, more preferably about; 12 to about 5:1;
    wherein the weight ratio of the total amount of silicone elastomer to the total amount of mineral thickening agent (silicone elastomer: mineral thickening agent) is about 1:1 to about 5:1, preferably about 1.1:1 to about 4:1, more preferably about 1.2:1 to about 4:1;
    all percentages by weight are based on the total weight of the cosmetic composition.

The cosmetic composition may also optionally include (or optionally exclude), for example, one or more non-volatile fatty substances, inorganic pigments, organic colorants, soft focus powder, water-soluble solvents, non-mineral thickening agents, surfactants (i.e., nonionic, amphoteric, anionic, or cationic), preservatives, fragrances, salts, etc. Many of these optionally constituents are described in more detail above, under their respective headings.

The cosmetic compositions may be aqueous compositions or anhydrous (or essentially anhydrous) compositions. In some instances, the cosmetic compositions are anhydrous or essentially anhydrous (or substantially anhydrous). In some instances the cosmetic compositions are aqueous.

When the cosmetic compositions are aqueous compositions, the total amount of water in the cosmetic composition can vary but is typically 5 to about 40 wt. %, based on the total weight of the cosmetic composition. The total amount of water may be 5 to about 35 wt. %, 5 to about 30 wt. %, 5 to about 25 wt. %, 5 to about 20 wt. %, about 6 to about 40 wt. %, about 6 to about 35 wt. %, about 6 to about 30 wt. %, about 6 to about 25 wt. %, about 6 to about 20 wt. %, about 8 to about 40 wt. %, about 8 to about 35 wt. %, about 8 to about 30 wt. %, about 8 to about 25 wt. %, or about 8 to about 20 wt. %, based on the total weight of the cosmetic composition.

In one embodiment, cosmetic compositions according to the instant disclosure comprise or consist of:
  about 30 to about 85 wt. %, preferably about 35 to about 80 wt. %, more preferably about 40 to about 75 wt. % of one or more volatile hydrocarbon oils, preferably, one or more volatile hydrocarbon oils are selected from branched C8 to C16 alkanes, such as, for example, isoparaffin, isohexadecane, isododecane, isodecane, undecane, tridecane, dodecane, and a mixture thereof;
  about 1 to about 20 wt. %, preferably about 1 to about 15 wt. %, more preferably about 1 to about 10 wt. % of one or more mineral thickening agents, preferably one or more optionally modified silicas and/or one or more optionally modified clays, in particular, hydrophobic silica aerogels (e.g., silica silylate) and/or organophilic modified clays (e.g., organophilic modified hectorites such as disteardimonium hectorite);
  about 1 to about 40 wt. %, preferably about 1 to about 30 wt. %, more preferably about 5 to about 25 wt. % of one or more non-emulsifying silicone elastomers, such as cross-linked silicone elastomers selected from dimethicone crosspolymer, (dimethicone/vinyl dimethicone) crosspolymer, (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and a mixture thereof, preferably dimethicone crosspolymer;
  optionally, about 1 to about 30 wt. %, preferably about 1 to about 25 wt. %, more preferably about 1 to about 20 wt. % of one or more emulsifying silicone elastomers, for example, one or more polyoxyalkylenated silicone elastomers, polyglycerolated silicone elastomers, and a mixture thereof;
  at least 5 wt. %, preferably at least 5 wt. % to about 30 wt. %, more preferably about 6 wt. % to about 25 wt. % of one or more hydrophobic film forming polymers, for instance block ethylenic copolymers, vinyl polymers comprising at least one carbosilxane dendrimer, based unit, silicone acrylate copolymers, and a mixture thereof, preferably acrylates/isobornyl acrylate copolymer;
  optionally, about 0.01 to about 10 wt. %, preferably about 0.1 to about 10 wt. %, more preferably about 0.1 to about 5 wt. % of one or more inorganic pigments, for example one or more inorganic pigments selected from titanium dioxide, zirconium oxide, cerium oxide, zinc oxide, iron oxide, alumina, aluminum hydroxide, chromium oxide, manganese violet, ultramarine blue, chromium hydrate, ferric blue, aluminum powder, copper powder, silver powder, gold powder, barium sulfate, carbon black, and mixtures thereof;

optionally, about 0.1 to about 20 wt. %, about 0.5 to about 15 wt. %, or about 1 to about 10 wt. % of soft focus powder, for example, talc, mica, titanated mica, alumina, aluminum silicate, silica which may or may not be coated, fumed silica, polyamide, methyl methacrylate crosspolymer, poly(methyl (meth)acrylate), polyethylene powder, polymethylsilsesquioxane powder, nylon-12 fluorescent brightener salt (and) polyvinylalcohol crosspolymer, or a mixture thereof (preferably selected from methyl methacrylate crosspolymer, nylon-12 fluorescent brightener 230 salt, and polyvinylalcohol crosspolymer); and optionally, one or more organic colorants, one or more water-soluble solvents, one or more non-mineral thickening agents, or a mixture thereof;

wherein the weight ratio of the total amount of hydrophobic film forming polymers to the total amount of mineral thickening agent (film forming polymers: mineral thickening agent) is about 1:1 to about 8:1, preferably about 1.1:1 to about 7:1, more preferably about; 12 to about 5:1;

wherein the weight ratio of the total amount of silicone elastomer to the total amount of mineral thickening agent (silicone elastomer: mineral thickening agent) is about 1:1 to about 5:1, preferably about 1.1:1 to about 4:1, more preferably about 1.2:1 to about 4:1;

all percentages by weight are based on the total weight of the cosmetic composition.

The cosmetic compositions may be aqueous compositions or anhydrous (or essentially anhydrous) compositions. In some instances, the cosmetic compositions are anhydrous or essentially anhydrous (or substantially anhydrous). In some instances the cosmetic compositions are aqueous.

When the cosmetic compositions are aqueous compositions, the total amount of water in the cosmetic composition can vary but is typically 5 to about 40 wt. %, based on the total weight of the cosmetic composition. The total amount of water may be 5 to about 35 wt. %, 5 to about 30 wt. %, 5 to about 25 wt. %, 5 to about 20 wt. %, about 6 to about 40 wt. %, about 6 to about 35 wt. %, about 6 to about 30 wt. %, about 6 to about 25 wt. %, about 6 to about 20 wt. %, about 8 to about 40 wt. %, about 8 to about 35 wt. %, about 8 to about 30 wt. %, about 8 to about 25 wt. %, or about 8 to about 20 wt. %, based on the total weight of the cosmetic composition.

In one embodiment, cosmetic compositions according to the instant disclosure are anhydrous or essentially anhydrous, and comprise or consist of:

about 30 to about 85 wt. %, preferably about 35 to about 80 wt. %, more preferably about 40 to about 75 wt. % of one or more volatile hydrocarbon oils selected from isoparaffin, isohexadecane, isododecane, isodecane, undecane, tridecane, dodecane, and a mixture thereof, preferably selected from isododecane and isoparaffin (e.g., C8-9 isoparaffin);

about 1 to about 20 wt. %, preferably about 1 to about 15 wt. %, more preferably about 1 to about 10 wt. % of one or more mineral thickening agents selected from hydrophobic silica aerogels (e.g., silica silylate) and/or organophilic modified clays (e.g., organophilic modified hectorites such as disteardimonium hectorite);

about 1 to about 40 wt. %, preferably about 1 to about 30 wt. %, more preferably about 5 to about 25 wt. % of one or more non-emulsifying silicone elastomers, such as cross-linked silicone elastomers selected from dimethicone crosspolymer, (dimethicone/vinyl dimethicone) crosspolymer, (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and a mixture thereof, preferably dimethicone crosspolymer;

about 1 to about 30 wt. %, preferably about 1 to about 25 wt. %, more preferably about 1 to about 20 wt. % of one or more emulsifying silicone elastomers, for example, one or more polyoxyalkylenated silicone elastomers, polyglycerolated silicone elastomers, and a mixture thereof;

at least 5 wt. %, preferably at least 5 wt. % to about 30 wt. %, more preferably about 6 wt. % to about 25 wt. % of one or more hydrophobic film forming polymers, for instance block ethylenic copolymers, vinyl polymers comprising at least one carbosilxane dendrimer, based unit, silicone acrylate copolymers, and a mixture thereof, preferably acrylates/isobornyl acrylate copolymer;

5 to about 35 wt. %, preferably about 6 to about 30 wt. %, more preferably about 10 to about 25 wt. % of water;

optionally, about 0.01 to about 10 wt. %, preferably about 0.1 to about 10 wt. %, more preferably about 0.1 to about 5 wt. % of one or more inorganic pigments, for example one or more inorganic pigments selected from titanium dioxide, zirconium oxide, cerium oxide, zinc oxide, iron oxide, alumina, aluminum hydroxide, chromium oxide, manganese violet, ultramarine blue, chromium hydrate, ferric blue, aluminum powder, copper powder, silver powder, gold powder, barium sulfate, carbon black, and mixtures thereof;

optionally, about 0.1 to about 20 wt. %, about 0.5 to about 15 wt. %, or about 1 to about 10 wt. % of methyl methacrylate crosspolymer, poly(methyl (meth)acrylate), polyethylene powder, polymethylsilsesquioxane powder, nylon-12 fluorescent brightener salt (and) polyvinylalcohol crosspolymer, or a mixture thereof (preferably methyl methacrylate crosspolymer and/or nylon-12 fluorescent brightener 230 salt, and polyvinylalcohol crosspolymer); and optionally, one or more non-volatile fatty substances, one or more organic colorants, one or more water-soluble solvents, one or more non-mineral thickening agents, or a mixture thereof;

wherein the weight ratio of the total amount of hydrophobic film forming polymers to the total amount of mineral thickening agent (film forming polymers: mineral thickening agent) is about 1:1 to about 8:1, preferably about 1.1:1 to about 7:1, more preferably about; 12 to about 5:1;

wherein the weight ratio of the total amount of silicone elastomer to the total amount of mineral thickening agent (silicone elastomer: mineral thickening agent) is about 1:1 to about 5:1, preferably about 1.1:1 to about 4:1, more preferably about 1.2:1 to about 4:1;

all percentages by weight are based on the total weight of the cosmetic composition.

In one embodiment, cosmetic compositions according to the instant disclosure are aqueous compositions, and comprise or consist of:

about 30 to about 85 wt. %, preferably about 35 to about 80 wt. %, more preferably about 40 to about 75 wt. % of one or more volatile hydrocarbon oils selected from isoparaffin, isohexadecane, isododecane, isodecane, undecane, tridecane, dodecane, and a mixture thereof, preferably selected from isododecane and isoparaffin (e.g., C8-9 isoparaffin);

about 1 to about 20 wt. %, preferably about 1 to about 15 wt. %, more preferably about 1 to about 10 wt. % of one or more mineral thickening agents selected from hydrophobic silica aerogels (e.g., silica silylate) and/or organophilic modified clays (e.g., organophilic modified hectorites such as disteardimonium hectorite);

about 1 to about 40 wt. %, preferably about 1 to about 30 wt. %, more preferably about 5 to about 25 wt. % of one or more non-emulsifying silicone elastomers, such as cross-linked silicone elastomers selected from dimethicone crosspolymer, (dimethicone/vinyl dimethicone) crosspolymer, (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and a mixture thereof, preferably dimethicone crosspolymer; and at least 5 wt. %, preferably at least 5 wt. % to about 30 wt. %, more preferably about 6 wt. % to about 25 wt. % of one or more hydrophobic film forming polymers, for instance block ethylenic copolymers, vinyl polymers comprising at least one carbosilxane dendrimer, based unit, silicone acrylate copolymers, and a mixture thereof, preferably acrylates/isobornyl acrylate copolymer;

optionally, about 0.01 to about 10 wt. %, preferably about 0.1 to about 10 wt. %, more preferably about 0.1 to about 5 wt. % of one or more inorganic pigments, for example one or more inorganic pigments selected from titanium dioxide, zirconium oxide, cerium oxide, zinc oxide, iron oxide, alumina, aluminum hydroxide, chromium oxide, manganese violet, ultramarine blue, chromium hydrate, ferric blue, aluminum powder, copper powder, silver powder, gold powder, barium sulfate, carbon black, and mixtures thereof;

optionally, about 0.1 to about 20 wt. %, about 0.5 to about 15 wt. %, or about 1 to about 10 wt. % of methyl methacrylate crosspolymer, poly(methyl (meth)acrylate), polyethylene powder, polymethylsilsesquioxane powder, nylon-12 fluorescent brightener salt (and) polyvinylalcohol crosspolymer, or a mixture thereof (preferably methyl methacrylate crosspolymer and/or nylon-12 fluorescent brightener 230 salt, and polyvinylalcohol crosspolymer); and optionally, one or more non-volatile fatty substances, one or more organic colorants, one or more water-soluble solvents, one or more non-mineral thickening agents, or a mixture thereof;

wherein the weight ratio of the total amount of hydrophobic film forming polymers to the total amount of mineral thickening agent (film forming polymers: mineral thickening agent) is about 1:1 to about 8:1, preferably about 1.1:1 to about 7:1, more preferably about; 12 to about 5:1;

wherein the weight ratio of the total amount of silicone elastomer to the total amount of mineral thickening agent (silicone elastomer: mineral thickening agent) is about 1:1 to about 5:1, preferably about 1.1:1 to about 4:1, more preferably about 1.2:1 to about 4:1;

all percentages by weight are based on the total weight of the cosmetic composition.

Implementation of the present disclosure is provided by way of the following examples. The examples serve to illustrate the technology without being limiting in nature.

Example 1

Anhydrous Compostions

|  | INCI US | A | B | C | D | E | F | G | H |
|---|---|---|---|---|---|---|---|---|---|
| Volatile Hydrocarbon Oil | ISODODECANE | 48.3 | 38.6 | 38.7 | 60.9 | 59.6 | 77.1 | 38.4 | 36.9 |
|  | C8-9 ISOPARAFFIN | 29.8 | 39.6 | 42 |  |  |  | 34.4 | 39.6 |
| Mineral Thickening Agent | SILICA SILYLATE | 3.9 | 3.9 | 3 | 2.7 | 2.7 | 3 | 2.5 | 3.9 |
| Silicone Elastomer (non-emulsifying) | DIMETHICONE CROSSPOLYMER | 5.8 | 5.8 | 6.3 | 4 | 4 | 10.2 | 5.8 | 5.4 |
| Hydrophobic Film-Forming Polymers | ACRYLATES/ISOBORNYL ACRYLATE COPOLYMER | 12.2 | 12.2 | 10 | 11.7 | 11.7 | 9.7 | 12.2 | 12.2 |
| Ratio (Film-Forming Polymers/Mineral Thickener) |  | 3.1 | 3.1 | 3.3 | 4.3 | 4.3 | 3.2 | 4.6 | 3.1 |
| Ratio (Silicone Elastomer/Mineral Thickener) |  | 1.5 | 1.5 | 2.1 | 1.5 | 1.5 | 3.4 | 2.3 | 1.4 |
| Inorganic Pigments | IRON OXIDES, ALUMINA, TITANIUM DIOXIDE, AND/OR ALUMINUM HYDROXIDE, ETC. |  |  |  |  | ≤5 |  |  | ≤5 |
| Soft Focus Particles | METHYL METHACRYLATE CROSSPOLYMER |  |  |  |  |  |  | 1.8 |  |
| Water-Soluble Solvent | GLYCERIN |  |  |  |  | 20.7 | 20.7 |  |  |
| Fatty Substance | PETROLATUM |  |  |  |  |  |  | 5 |  |

Example 2

Aqueous Compositions

|  | INCI US | I | J | K | L | M | N | O | P |
|---|---|---|---|---|---|---|---|---|---|
|  | ISODODECANE | 23 | 61 | 31 | 31 | 31 | 31 | 29 | 29 |
| Volatile Hydrocarbon Oil | C8-9 ISOPARAFFIN | 18 |  | 28 | 32 | 31 | 26 | 32 | 26 |
| Mineral Thickening Agent | SILICA SILYLATE, AND/OR DISTEARDIMONIUM HECTORITE (and) PROPYLENE CARBONATE | 2 | 2.7 | 2.5 | 3.1 | 2 | 2 | 3.1 | 2 |

-continued

| | | | | | | | | |
|---|---|---|---|---|---|---|---|---|
| Silicone Elastomer (non-emulsifying) | DIMETHICONE CROSSPOLYMER | | 3.6 | 3.6 | 4.6 | 4.6 | 4.6 | 4.3 | 4.3 |
| Silicone Elastomer (emulsifying) | PEG-15/LAURYL POLYDIMETHYLSILOXYETHYL DIMETHICONE CROSSPOLYMER, PEG/PPG-18/18 DIMETHICONE, AND/OR LAURYL PEG-9 POLYDIMETHYLSILOXYETHYL DIMETHICONE | 7.5 | | | 2 | 2 | 2 | 2 | 2 |
| Hydrophobic Film-Forming Polymers | ACRYLATES/ISOBORNYL ACRYLATE COPOLYMER | 5 | 11.7 | 15 | 9.8 | 9.8 | 9.8 | 9.8 | 9.8 |
| Ratio (Film-Forming Polymers/Mineral Thickener) | | 2.5 | 4.3 | 6 | 3.1 | 4.9 | 4.9 | 3.2 | 4.9 |
| Ratio (Silicone Elastomer/Mineral Thickener) | | 3.8 | 1.5 | 1.4 | 2.1 | 3.3 | 3.3 | 2.0 | 3.2 |
| Inorganic Pigments | IRON OXIDES, TITANIUM DIOXIDE, MICA, TIN OXIDE, BORON NITRIDE, AND/OR ALUMINUM HYDROXIDE, ETC. | | | | | | | ≤5 | ≤5 |
| Soft Focus Particles | METHYL METHACRYLATE CROSSPOLYMER, NYLON-12 FLUORESCENT BRIGHTENER 230 SALT, AND/OR POLYVINYLALCOHOL CROSSPOLYMER. | | | | | 1.5 | 1.5 | | 1.5 |
| Silicone Oil | DIMETHICONE | | | | | 1.5 | 1.5 | 1.5 | 1.5 |
| Fatty Substance | PETROLATUM | | | | | | 5 | | 5 |
| Misc. | EMOLLIENTS, PRESERVATIVES, SALTS, ETC. | ≤2 | ≤2 | ≤2 | ≤2 | ≤2 | ≤2 | ≤2 | ≤2 |
| Water-soluble solvent | GLYCERIN | | 10.3 | | | | | | |
| Water | WATER | 40 | 10.3 | 20 | 16 | 16 | 16 | 16 | 16 |

| | INCI US | Q | R | S | T | U | V | W |
|---|---|---|---|---|---|---|---|---|
| Volatile Hydrocarbon Oil | ISODODECANE | 27 | 31 | 31 | 31 | 31 | 33 | 31 |
| | C8-9 ISOPARAFFIN | 32 | 32 | 31 | 31 | 31 | 30 | 30 |
| Mineral Thickening Agent | SILICA SILYLATE, AND/OR DISTEARDIMONIUM HECTORITE (and) PROPYLENE CARBONATE | 3.1 | 3.1 | 3.1 | 3.1 | 3.1 | 3.4 | 3.1 |
| Silicone Elastomer (non-emulsfiying) | DIMETHICONE CROSSPOLYMER | 3.7 | 4.6 | 4.6 | 4.6 | 4.6 | 4.6 | 4.6 |
| Silicone Elastomer (emulsfiying) | PEG-15/LAURYL POLYDIMETHYLSILOXYETHYL DIMETHICONE CROSSPOLYMER, PEG/PPG-18/18 DIMETHICONE, AND/OR LAURYL PEG-9 POLYDIMETHYLSILOXYETHYL DIMETHICONE | 2 | 2 | 2 | 2 | 2 | 2 | 2 |
| Hydrophobic Film-Forming Polymers | ACRYLATES/ISOBORNYL ACRYLATE COPOLYMER | 9.8 | 9.8 | 9.7 | 9.7 | 9.8 | 9.8 | 9.8 |
| Ratio (Film-Forming Polymers/Mineral Thickener) | | 3.2 | 3.2 | 3.1 | 3.1 | 3.2 | 2.9 | 3.2 |
| Ratio (Silicone Elastomer/Mineral Thickener) | | 1.8 | 2.1 | 2.1 | 2.1 | 2.1 | 1.9 | 2.1 |
| Inorganic Pigments | IRON OXIDES, TITANIUM DIOXIDE, MICA, TIN OXIDE, BORON NITRIDE, AND/OR ALUMINUM HYDROXIDE, ETC. | ≤5 | | ≤5 | | 0.5 | | |
| Soft Focus Particles | METHYL METHACRYLATE CROSSPOLYMER, NYLON-12 FLUORESCENT BRIGHTENER 230 SALT, AND/OR POLYVINYLALCOHOL CROSSPOLYMER. | | | | | 0.5 | | |
| Suspending agent | POLYHYDROXYSTEARIC ACID | | | | | | | 2 |
| Silicone Oil | DIMETHICONE | 1.5 | 1.5 | 1.5 | 1.5 | 1.5 | 1.5 | 1.5 |
| Misc. | EMOLLIENTS, PRESERVATIVES, SALTS, ETC. | ≤2 | ≤2 | ≤2 | ≤2 | ≤2 | ≤2 | ≤2 |
| Water | WATER | 16 | 16 | 16 | 16 | 16 | 16 | 16 |

Example 3

Comparative Compositions

| | INCI US | Comparative 1 No Mineral Thickener | Comparative 2 No Silicone Elastomer |
|---|---|---|---|
| Volatile Hydrocarbon Oil | ISODODECANE | 58 | 44.2 |
| | C8-9 ISOPARAFFIN | 19.8 | 34.3 |
| Mineral Thickening Agent | SILICA SILYLATE | | 5.2 |
| Silicone Elastomer | DIMETHICONE CROSSPOLYMER | 10 | |

-continued

|  | INCI US | Comparative 1 No Mineral Thickener | Comparative 2 No Silicone Elastomer |
|---|---|---|---|
| Hydrophobic Film-Forming Polymers | ACRYLATES/ ISOBORNYL ACRYLATE COPOLYMER | 12.2 | 16.3 |
| Water | WATER | | |

Example 4

Performance Testing

Inventive Composition B (of Example 1) and Comparative Compositions 1 and 2 (Example 3) were evaluated to determine their usefulness for improving the appearance of skin. The ingredients of the compositions are provided in the table below for ease of reference.

|  | INCI US | B | C-1 | C-2 |
|---|---|---|---|---|
| Volatile Hydrocarbon Oil | ISODODECANE | 38.6 | 58 | 44.2 |
|  | C8-9 ISOPARAFFIN | 39.6 | 19.8 | 34.3 |
| Mineral Thickening Agent | SILICA SILYLATE | 3.9 |  | 5.2 |
| Silicone Elastomer | DIMETHICONE CROSSPOLYMER | 5.8 | 10 |  |
| Hydrophobic Film-Forming Polymers | ACRYLATES/ ISOBORNYL ACRYLATE COPOLYMER | 12.2 | 12.2 | 16.3 |
| Ratio (Film-Forming Polymers/ Mineral Thickener) |  | 3.1 | NA | 3.1 |
| Ratio (Silicone Elastomer/ Mineral Thickener) |  | 1.5 | NA | 0 |

Inventive Composition B provided a significant reduction of wrinkles that was sustained for several hours without cracking. Comparative Composition C1, however, provided no immediate reduction in wrinkles and became sticky with time. Comparative Composition C2 provided a significant reduction of wrinkles but developed unpleasant cracking with time. The data shows that both a mineral thickening agent and a silicone elastomer are needed to ensure that the compositions provide immediate wrinkle reduction that is sustained for a long period without developing unpleasant cracking. Compositions B, C-1, and C-2 differ with respect to the amount of isododecane, isoparaffin, and acrylate/ isobornyl acrylate copolymer. These differences, however, contribute little, if any, to the functional differences reported above for the compositions (e.g., durability, stickiness, cracking). The differences were required to ensure that all three compositions had comparable viscosities. For example, if the removed silicone elastomer (dimethicone crosspolymer) in Comparative Composition C2 is replaced by only mineral thickening agent (silica silylate), a solid is formed. On the other hand, if the removed silicone elastomer (dimethicone crosspolymer) in Comparative Composition C2 is replaced by only volatile hydrocarbon oil (isododecane), the composition is too runny (liquid). Therefore, the amounts of the various ingredients in the comparative compositions were adjusted to ensure a comparative viscosity with Inventive Composition B. For Comparative Composition C-2, the ratio of film-forming polymers to mineral thickener, however, was maintained (at 3.1) to correlate with Inventive Composition B. Ratios cannot be maintained for Comparative Composition C1 (because it does not contain mineral thickening agent). Therefore, silicone elastomer was added to compensate for the absence of the mineral thickening agent (silica silylate). The raw material for the silicone elastomer, however, contains 82% isododecane. Therefore, the amount of isododecane is necessarily increased with the addition of the silicone elastomer.

Example 5

Comparative with Commercial Benchmark

Inventive Compositions B and C (Example 1) and I, K, and M (Example 2) were tested on a panel of 6 individuals having grade 4 under eye wrinkles (based on Atlas' scores of 0 to 5) and compared with a commercial benchmark product. The individuals' faces were cleansed and the skin allowed to completely dry and acclimate for 10 minutes. After 10 minutes, a standard facial moisturizing composition was applied to the skin. The moisturizing composition was applied in order to mimic a regular skin care routine. Approximately 2 minutes after application of the moisturizing composition, the composition was applied full face. The panelists were evaluated by a cosmetologist at baseline, 10 min., 30 min., 3 hours, and 6 hours. Each of the applicable attributes (forehead lines, *glabella* lines, crow's feet, under eye wrinkles, under eye bags, nasolabials, marionettes, ptosis and pores) were graded based on a Skin Aging Atlas on a scale of 0 to 5 (none to severe). The results are summarized in the tables below.

| FOREHEAD | | | | | |
|---|---|---|---|---|---|
| Time/ Composition | $T_0$ | $10_{min}$ | $30_{min}$ | $3_{hrs}$ | $6_{hrs}$ |
| B | 3.00 | 1.33 | 1.17 | 1.17 | 1.50 |
| C | 3.00 | 1.75 | 2.25 | 2.25 | 2.75 |
| I | 3.00 | 1.50 | 1.50 | 1.75 | 1.75 |
| K | 3.00 | 1.75 | 1.50 | 1.75 | 2.50 |
| M | 2.50 | 1.67 | 1.50 | 1.83 | 2.33 |
| Benchmark | 3.00 | 2.25 | 1.75 | 2.25 | 2.50 |

| GLABELLA LINES | | | | | |
|---|---|---|---|---|---|
| Time/ Composition | $T_0$ | $10_{min}$ | $30_{min}$ | $3_{hrs}$ | $6_{hrs}$ |
| B | 3.00 | 1.50 | 1.17 | 1.33 | 1.50 |
| C | 3.25 | 2.75 | 2.75 | 2.50 | 3.25 |
| I | 3.25 | 2.00 | 2.00 | 2.25 | 2.50 |
| K | 3.25 | 2.50 | 2.75 | 2.75 | 3.00 |
| M | 2.00 | 1.00 | 0.83 | 1.17 | 1.17 |
| Benchmark | 3.25 | 3.00 | 2.25 | 3.25 | 3.25 |

| CROW'S FEET | | | | | |
|---|---|---|---|---|---|
| Time/ Composition | $T_0$ | $10_{min}$ | $30_{min}$ | $3_{hrs}$ | $6_{hrs}$ |
| B | 2.83 | 0.33 | 0.33 | 1.00 | 1.50 |
| C | 3.00 | 1.75 | 2.00 | 2.25 | 2.50 |
| I | 3.00 | 1.25 | 1.25 | 2.00 | 2.25 |
| K | 3.00 | 1.75 | 2.00 | 2.50 | 2.25 |
| M | 3.17 | 1.00 | 0.83 | 1.67 | 2.00 |
| Benchmark | 3.25 | 2.25 | 2.00 | 2.75 | 2.75 |

| UNDER EYE WRINKLES | | | | | |
|---|---|---|---|---|---|
| Time/Composition | $T_0$ | $10_{min}$ | $30_{min}$ | $3_{hrs}$ | $6_{hrs}$ |
| B | 3.67 | 1.17 | 1.00 | 1.00 | 1.33 |
| C | 3.75 | 2.50 | 2.00 | 2.00 | 2.00 |
| I | 3.75 | 1.75 | 1.50 | 1.50 | 1.75 |
| K | 3.75 | 1.75 | 2.00 | 2.25 | 2.25 |
| M | 3.33 | 1.33 | 1.00 | 1.33 | 2.17 |
| Benchmark | 3.75 | 2.50 | 2.75 | 3.25 | 3.25 |

| UNDER EYE BAGS | | | | | |
|---|---|---|---|---|---|
| Time/Composition | $T_0$ | $10_{min}$ | $30_{min}$ | $3_{hrs}$ | $6_{hrs}$ |
| B | 2.33 | 0.33 | 0.00 | 0.50 | 0.67 |
| C | 2.00 | 1.75 | 2.00 | 1.75 | 2.00 |
| I | 2.00 | 1.25 | 1.00 | 1.00 | 1.00 |
| K | 2.00 | 1.50 | 1.50 | 1.75 | 1.75 |
| M | 3.83 | 2.17 | 1.83 | 2.33 | 2.67 |
| Benchmark | 2.00 | 1.50 | 1.00 | 1.25 | 1.50 |

| NASIOLABIALS | | | | | |
|---|---|---|---|---|---|
| Time/Composition | $T_0$ | $10_{min}$ | $30_{min}$ | $3_{hrs}$ | $6_{hrs}$ |
| B | 3.33 | 2.17 | 2.33 | 2.67 | 2.83 |
| C | 3.75 | 3.00 | 2.50 | 3.25 | 3.50 |
| I | 3.75 | 3.25 | 3.25 | 3.25 | 3.25 |
| K | 3.75 | 3.00 | 3.00 | 3.00 | 3.00 |
| M | 3.50 | 2.50 | 2.00 | 2.67 | 2.67 |
| Benchmark | 3.75 | 3.75 | 3.00 | 3.75 | 3.75 |

| MARIONNETTES | | | | | |
|---|---|---|---|---|---|
| Time/Composition | $T_0$ | $10_{min}$ | $30_{min}$ | $3_{hrs}$ | $6_{hrs}$ |
| B | 2.67 | 1.50 | 1.50 | 2.50 | 2.67 |
| C | 2.50 | 2.00 | 2.25 | 2.25 | 2.50 |
| I | 2.50 | 1.50 | 1.75 | 2.00 | 2.00 |
| K | 2.50 | 2.00 | 2.00 | 2.00 | 2.25 |
| M | 3.67 | 3.00 | 2.67 | 3.00 | 3.50 |
| Benchmark | 3.00 | 2.25 | 1.75 | 2.25 | 2.25 |

| PTOSIS | | | | | |
|---|---|---|---|---|---|
| Time/Composition | $T_0$ | $10_{min}$ | $30_{min}$ | $3_{hrs}$ | $6_{hrs}$ |
| B | 2.17 | 1.00 | 1.00 | 2.00 | 1.83 |
| C | 2.00 | 1.50 | 1.50 | 1.50 | 1.75 |
| I | 2.00 | 1.00 | 1.00 | 1.25 | 1.25 |
| K | 2.00 | 2.00 | 2.00 | 2.00 | 2.00 |
| M | 3.00 | 2.67 | 2.00 | 3.00 | 3.00 |
| Benchmark | 2.00 | 1.50 | 1.25 | 1.50 | 1.75 |

| PORES | | | | | |
|---|---|---|---|---|---|
| Time/Composition | $T_0$ | $10_{min}$ | $30_{min}$ | $3_{hrs}$ | $6_{hrs}$ |
| B | 2.17 | 0.50 | 0.50 | 0.50 | 0.67 |
| C | 2.25 | 1.00 | 0.75 | 0.75 | 1.25 |
| I | 2.25 | 1.00 | 1.25 | 1.25 | 1.25 |
| K | 2.25 | 2.25 | 0.75 | 0.75 | 0.75 |
| M | 2.33 | 0.67 | 0.67 | 0.83 | 0.83 |
| Benchmark | 2.25 | 1.25 | 1.00 | 1.50 | 1.33 |

The results show that application of Inventive Compositions, B, C, 1, K, and M significantly improved (reduced the appearance of) under eye wrinkles and nasolabials compared to the Comparative Commercial Benchmark, with improvements lasting for at least 6 hours. The results also show that application of Inventive Compositions, B, C, 1, K, and M generally improved (reduced the appearance of) eye bags, crow's feet, glabellar lines, forehead lines, marionettes, ptosis and pores compared to the Comparative Commercial Benchmark.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a particular component may be considered both an inorganic pigment and a soft focus powder. If a particular composition includes both an inorganic pigment and a soft focus powder, a single ingredient will serve as only the inorganic pigment or only the soft focus powder (a single ingredients cannot serve as both the inorganic pigment and the soft focus powder).

Mineral thickening agents can be distinguished from inorganic pigment because, for purposes of the instant disclosure, mineral thickening agents provide thickening properties to the compositions, whereas inorganic pigments do not provide appreciable thickening but instead provide coloring properties to the compositions.

The salts referred to throughout the disclosure may include salts having a counter-ion such as an alkali metal, alkaline earth metal, or ammonium counter-ion. This list of counter-ions, however, is non-limiting.

The term "treat" (and its grammatical variations) as used herein refers to the application of the compositions of the present disclosure onto the surface of keratinous substrates such as skin, in particular, the skin of the head, face, and neck.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. An essentially anhydrous cosmetic composition comprising:
    (a) about 40 to about 80 wt. % of one or more volatile hydrocarbon oils selected from isoparaffin, isohexadecane, isododecane, isodecane, undecane, tridecane, dodecane, or mixtures thereof;
    (b) about 2 to about 5 wt. % of silica silylate;
    (c) 2 to about 15 wt. % of dimethicone crosspolymer;
        wherein (c) and (b) are in a weight ratio of 1.2:1 to 4:1 ((c):(b));
    (d) at least 5 wt. % of acrylates/isobornyl acrylate copolymer;
        wherein (d) and (b) are in a weight ratio of 1:1 to 5:1 ((d):(b));
    (e) optionally, about 0.1 to about 5 wt. % of one or more inorganic pigments;
    (f) optionally, about 0.1 to about 5 wt. % of soft-focus particles; and
        wherein the composition comprises less than 2 wt. % of water, and
        all percentages by weight are based on a total weight of the composition.

2. The composition of claim 1 comprising the one or more inorganic pigments.

3. The composition of claim 2, wherein the one or more inorganic pigments are selected from titanium dioxide, zirconium oxide, cerium oxide, zinc oxide, iron oxide, alumina, aluminum hydroxide, chromium oxide, manganese violet, ultramarine blue, chromium hydrate, ferric blue, aluminum powder, copper powder, silver powder, gold powder, barium sulfate, carbon black, mixtures thereof.

4. The composition of claim 1 comprising the soft-focus particles.

5. The composition of claim 4, wherein the soft-focus particles are methyl methacrylate crosspolymer.

6. The composition of claim 1, further comprising:
    (g) one or more water-soluble solvents.

7. The composition of claim 6, wherein the one or more water-soluble solvents are selected from ethyl alcohol, isopropyl alcohol, propyl alcohol, ethylene glycol, propylene glycol, butylene glycol, hexylene glycol, propane diol, glycerin, or mixtures thereof.

8. The composition of claim 1, wherein the composition has a viscosity of about 25 Pa·s to about 5,000 Pa·s measured at 25° C. and 1 s$^{-1}$ shear.

9. The composition of claim 1, wherein the dimethicone crosspolymer is in an amount from about 5 to 10 wt. %.

10. The composition of claim 1, wherein the acrylates/isobornyl acrylate copolymer is in an amount from about 6 to about 15 wt. %.

11. The composition of claim 1, wherein the composition further comprises one or more non-volatile fatty substances.

12. A cosmetic composition comprising:
    (a) about 40 to about 80 wt. % of isoparaffin, isohexadecane, isododecane, isodecane, undecane, tridecane, dodecane, or mixtures thereof;
    (b) about 2 to about 5 wt. % of silica silylate;
    (c) about 5 to about 15 wt. % of dimethicone crosspolymer;
        wherein (c) and (b) are in a weight ratio of 1.4:1 to 4:1 ((c):(b));
    (d) about 6 to about 15 wt. % of acrylates/isobornyl acrylate copolymer;
        wherein (d) and (b) are in a weight ratio of 1.2:1 to 5:1 ((d):(b));

(e) optionally, about 0.1 to about 5 wt. % of one or more inorganic pigments;

(f) optionally, about 0.1 to about 5 wt. % of soft-focus particles; and wherein all percentages by weight are based on a total weight of the cosmetic composition.

13. The composition of claim 12 comprising the one or more inorganic pigments.

14. The composition of claim 13, wherein the one or more inorganic pigments are selected from titanium dioxide, zirconium oxide, cerium oxide, zinc oxide, iron oxide, alumina, aluminum hydroxide, chromium oxide, manganese violet, ultramarine blue, chromium hydrate, ferric blue, aluminum powder, copper powder, silver powder, gold powder, barium sulfate, carbon black, or mixtures thereof.

15. The composition of claim 12 comprising the soft-focus particles.

16. The composition of claim 15, wherein the soft-focus particles are methyl methacrylate crosspolymer.

17. The composition of claim 12, further comprising:

(g) one or more water-soluble solvents.

18. The composition of claim 17, wherein the one or more water-soluble solvents are selected from ethyl alcohol, isopropyl alcohol, propyl alcohol, ethylene glycol, propylene glycol, butylene glycol, hexylene glycol, propane diol, glycerin, or mixtures thereof.

19. A method for improving the appearance of skin comprising applying the cosmetic composition of claim 1 to the skin.

20. A method for improving the appearance of skin comprising applying the cosmetic composition of claim 12 to the skin.

\* \* \* \* \*